(12) United States Patent
Greene et al.

(10) Patent No.: US 10,583,166 B2
(45) Date of Patent: *Mar. 10, 2020

(54) ANTIGEN-BINDING PROTEINS COMPRISING RECOMBINANT PROTEIN SCAFFOLDS

(71) Applicant: The Trustees of the University of Pennsylvania, Philadelphia, PA (US)

(72) Inventors: Mark I. Greene, Penn Valley, PA (US); Hongtao Zhang, Paoli, PA (US); Xiaomin Song, Drexel Hill, PA (US); Ramachandran Murali, Beverly Hills, CA (US); Masahide Tone, Los Angeles, CA (US)

(73) Assignee: THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/587,441

(22) Filed: May 5, 2017

(65) Prior Publication Data

US 2017/0239324 A1    Aug. 24, 2017

Related U.S. Application Data

(60) Continuation of application No. 14/243,614, filed on Apr. 2, 2014, now Pat. No. 9,695,252, which is a division of application No. 13/262,060, filed as application No. PCT/US2010/029386 on Mar. 31, 2010, now Pat. No. 8,728,479.

(60) Provisional application No. 61/165,010, filed on Mar. 31, 2009.

(51) Int. Cl.

| C07K 19/00 | (2006.01) |
|---|---|
| A61K 39/395 | (2006.01) |
| G01N 33/53 | (2006.01) |
| A61K 38/16 | (2006.01) |
| A61K 49/00 | (2006.01) |
| C07K 14/705 | (2006.01) |
| C07K 16/28 | (2006.01) |
| C07K 1/22 | (2006.01) |

(52) U.S. Cl.
CPC .............. *A61K 38/16* (2013.01); *A61K 49/00* (2013.01); *C07K 1/22* (2013.01); *C07K 14/70596* (2013.01); *C07K 16/2896* (2013.01); *C07K 19/00* (2013.01); *G01N 33/53* (2013.01); *C07K 2319/30* (2013.01)

(58) Field of Classification Search
None
See application file for complete search history.

(56) References Cited

U.S. PATENT DOCUMENTS

| 5,684,146 | A  |   | 11/1997 | Okuno et al. |
|---|---|---|---|---|
| 5,831,012 | A  |   | 11/1998 | Nilsson et al. |
| 2004/0033511 | A1 | * | 2/2004 | Pfizenmaier ............ B82Y 5/00 |
|  |  |  |  | 435/6.18 |
| 2006/0120960 | A1 |   | 6/2006 | Deyev et al. |
| 2006/0159683 | A1 |   | 7/2006 | Pluckthun et al. |
| 2006/0263368 | A1 | * | 11/2006 | Rosenblum ........ A61K 41/0038 |
|  |  |  |  | 424/155.1 |
| 2008/0260757 | A1 |   | 10/2008 | Holt et al. |
| 2011/0020223 | A1 |   | 1/2011 | Abrahmsen et al. |
| 2012/0058114 | A1 |   | 3/2012 | Barbas, III |

FOREIGN PATENT DOCUMENTS

| WO |  | 00/69888 | A1 |   | 11/2000 |
|---|---|---|---|---|---|
| WO |  | 2005/003156 | A1 |   | 1/2005 |
| WO |  | 2006/074399 | A2 |   | 7/2006 |
| WO |  | 2007/062037 | A2 |   | 5/2007 |
| WO | WO | 2007/076923 |  | * | 7/2007 |
| WO | WO | 2009/000538 |  | * | 12/2008 |
| WO |  | 2010/120514 | A2 |   | 10/2010 |

OTHER PUBLICATIONS

Wriggers et al., Control of Protein Functional Dynamics by peptide Linkers, Biopolymers (Peptide Science), 2005, 80:736-746.

Tang et al., "Selection of Linkers for a Catalytic Single-chain Antibody Using Phage Display Technology," J. Biol. Chem., Jun. 28, 1996, 271(26), 15682-15686.

Stephens et al, Engagement of Glucocorticoid-Induced TNFR Family-Related Receptor on Effector T Cells by its Ligand Mediates Resistance to Suppression by CD4+CD25+T Cells, The Journal of Immunology, 2004, 173, 5008-5020.

Robinson et al., "Colloquium Paper: Optimizing the stability of single-chain proteins by linker length and composition mutagenesis," PNAS, May 26, 1998, 95(11), 5929-5934.

Park et al., "Rationally designed anti-HER2/neu peptide mimetic disables P185HER2/neu tyrosine kinases in vitro and in vivo," Nature Biotechnology, Feb. 2000, 18(2), 194-198.

Masuda et al., "AHNP-streptavidin: a tetrameric bacterially produced antibody surrogate fusion protein against p185her2/neu," Oncogene, Dec. 14, 2006, 25(59), 7740-7746.

Li et al., "Filamentous Bacteriophage Display of a Bifunctional Protein A" (Molecular Biology, 1998, 9:187-193.

Karlin et al., "Applications and statistics for multiple high-scoring segments in molecular sequences," PNAS, Jun. 15, 1993, 90(12), 5873-5877.

(Continued)

*Primary Examiner* — Laura B Goddard
(74) *Attorney, Agent, or Firm* — Riverside Law LLP

(57) ABSTRACT

Disclosed herein are recombinant protein scaffolds and recombinant multifunctional protein scaffolds for use in producing antigen-binding proteins In addition, nucleic acids encoding such recombinant protein scaffolds, recombinant multifunctional protein scaffolds, and antigen-binding proteins are provided Vectors and cells useful for expression of the described proteins are also provided, as are methods of use.

14 Claims, 9 Drawing Sheets

Specification includes a Sequence Listing.

(56) References Cited

OTHER PUBLICATIONS

Johnstone and Thorpe "Immunochemistry in Practice", 2nd Ed., Blackwell Scientific Publications, Oxford, 1987, pp. 49-50.
International Patent Application No. PCT/US2010/029386: International Search Report and Written Opinion dated Nov. 19, 2010, 13 pages.
Hosse et al, A new generation of protein display scaffolds for molecular recognition, Protein Science, 2006, 15:14-27.
Altschul et al., "Methods for assessing the statistical significance of molecular sequence features by using general scoring schemes," PNAS, Mar. 1990, 87(6), 2264-2268.

* cited by examiner

Classes of small antibody surrogates (SAbS):

I. SAbS with scaffold

II. SAbS with Fc function region

II. SAbS with scaffold and Fc function region

---

Legend:

Binding peptide region (e.g. AHNP, scFv, etc)

scaffold region (e.g. LZ domain, GITRL, etc)

Fc function region (e.g. ZZ domain, CH2 mimic, etc)

His-tag

Linker

ANTIGEN-BINDING PROTEINS COMPRISING RECOMBINANT PROTEIN SCAFFOLDS

CROSS REFERENCE TO RELATED APPLICATIONS

This application is a continuation of U.S. application Ser. No. 14/243,614, filed Apr. 2, 2014, which is a divisional of U.S. application Ser. No. 13/262,060, filed Dec. 15, 2011, issued as U.S. Pat. No. 8,728,479, which is the National Stage of International Application No. PCT/US2010/029386, filed Mar. 31, 2010, which claims the benefit of U.S. Provisional Application No. 61/165,010, filed Mar. 31, 2009, the disclosures of each of which are incorporated herein by reference in their entirety.

GOVERNMENT RIGHTS

This invention was made with government support under grant numbers 5 R01 CA055306-17 and 1 R01 CA149425-02 awarded by the National Institutes of Health. The government has certain rights in the invention.

BACKGROUND

Since hybridoma technology enabled long-lived hybridoma production of monoclonal antibodies in the mid-1970's, scientist and clinicians have been trying to harvest their therapeutic potential to treat diseases. Over the years, science has pushed back the frontiers of antibody technology, allowing for the development of chimeric antibodies, humanized antibodies, and immunologically functional antibody fragments, such as Fabs and diabodies. Today, there are numerous antibody therapeutics used to treat diseases such as cancer, infectious diseases, and autoimmune disorders, just to name a few. In addition to existing therapeutics, more are on the horizon and the scientific community is working feverishly to develop new and/or more effective antibody-based therapeutics.

While antibody therapeutics have proven successful in recent years, with at least 25 such therapeutics having gained FDA approval, they are not without drawbacks. Some drawbacks to antibodies include their large size (approximately 150 kD) and that they often require proper post-translational processing. The large size of antibodies can reduce their ability to target certain diseases, such as cancer or neurological disorders, which may require crossing the blood-brain barrier. The fact that many antibodies require proper post-translational processing by a eukaryotic cell often requires that antibody therapeutics be produced in, and subsequently purified from, mammalian cell culture, which can hinder total antibody production and increase production costs, relative to proteins produced in bacteria.

To overcome some of the drawbacks of antibodies, non-antibody synthetic proteins have been developed. Some examples of non-antibody synthetic proteins include antibody fragments, such as Fabs, scFvs, diabodies, Affibodies®, and Nanobodies®, to name a few. Proteins such as these, while smaller than antibodies and useful for some applications, often do not have the ability to interact with antibody receptors, such as the Fc receptor, expressed by immune effector cells, which can enhance the activity of the immune system.

To address some of the shortcomings of antibodies and non-antibody synthetic proteins, disclosed herein are protein scaffolds and multifunctional protein scaffolds for use in producing antigen-binding proteins.

SUMMARY

Described herein are protein scaffolds for use in producing antigen-binding proteins. A variety of protein scaffolds are described, as are a variety of functional attributes or characteristics that can be associated with the described protein scaffolds. Several of the disclosed protein scaffolds are made of at least one protein scaffold or framework segment that can be linked to at least one antigen-specific polypeptide sequence, known as a antigen-specific peptide, to form an antigen-binding protein. The scaffold proteins described herein can also be attached to polypeptides that confer desirable functional characteristics such as the ability to bind to the fragment crystallizable (Fc) region of an antibody or the ability to bind a particular antigen and an Fc receptor simultaneously. In addition, some of the scaffold protein segments may inherently possess these, or other, desired functional characteristics, which also allows them to be attached to other antigen-specific proteins to confer this activity. Some of the antigen-binding proteins resulting from the combination of the described scaffold protein constructs and an antigen-specific peptide that are described herein have the ability to bind a particular antigen and the Fc region of an antibody in addition to having a detectable label attached to the antigen-binding protein. Also disclosed are polynucleotides encoding the described protein scaffold or exemplary antigen-binding proteins, vectors encoding the described scaffold constructs or exemplary antigen-binding proteins, cells transformed with the disclosed vectors, and methods of treating, diagnosing, or preventing disease using the described antigen-binding proteins, and methods of detecting antigens of interest using the described antigen-binding proteins.

One embodiment of the protein scaffolds described herein, the LZ scaffold, includes a scaffold segment derived from a leucine zipper domain of the FOXP3 protein, which can be linked or combined with at least one antigen-specific peptide (SEQ ID NOs. 12-24) to form an antigen-binding protein. In one embodiment, the antigen-binding protein includes the LZ scaffold linked to an antigen-specific peptide, such as an Anti-Her2/neu Peptide (AHNP) (SEQ ID NO. 12) derived from the 4D5 antibody, to create an antigen-binding protein specific for the Her2/neu receptor. In another embodiment this antigen-binding protein, or an analogous antigen-binding protein specific for a different antigen, can include a detectable label, for example, an epitope tag, a fluorophore, a radio isotope, or an enzyme. One embodiment of such an antigen-binding protein can have an amino acid sequence of, or substantially similar to, SEQ ID NO. 5. It should be noted that many embodiments of the antigen-binding proteins described herein are exemplified using the antigen-specific peptide AHNP; however, any of the antigen-specific peptides disclosed herein (SEQ ID NOs. 12-24), as well as other such peptides known to those of skill in the art, can be used to produce antigen-binding proteins using the protein scaffolds described herein.

Another protein scaffold described herein, the CH2-mimic scaffold, includes a scaffold segment designed to imitate the CH2 domain of an antibody. This scaffold can be linked or combined with at least one antigen-specific peptide to form an antigen-binding protein. In one embodiment, this antigen-binding protein includes the CH2-mimic scaffold linked to an antigen-specific peptide, such as AHNP, to create an antigen-binding protein specific for the Her2/neu receptor. In another embodiment, this antigen-binding protein, or an analogous antigen-binding protein specific for a different antigen, can include a detectable label, for example, an epitope tag, a fluorophore, a radio isotope, or an enzyme. One embodiment of such an antigen-binding protein can have an amino acid sequence of, or substantially similar to, SEQ ID NO. 6. Alternative embodiments of such an antigen-binding protein can be produced using any of the antigen-specific peptides described in SEQ ID NOs. 13-24.

Described herein are also scaffolds for making antigen-binding proteins that can not only bind to a particular antigen, but can also bind to antibodies. Such antigen-binding proteins can have at least one protein segment that is capable of binding to the Fc region of an antibody. In some embodiments, the Fc-binding segment can also serve as a scaffold for an antigen-specific peptide. Such an antigen-binding protein can be produced by the combination of a protein scaffold derived from a portion of Protein A, a *Staphylococcus aureus* cell wall component that has the ability to bind to certain antibody isotypes, with an antigen-specific peptide. In one embodiment, this type of antigen-binding protein includes a ZZ scaffold (SEQ ID NO. 3), derived from a portion of Protein A, linked to AHNP. An additional embodiment of this protein, or an analogous antigen-binding protein specific for a different antigen, can also include a detectable label such as an epitope tag, a fluorophore, a radio isotope, or an enzyme (SEQ ID NO. 7). Alternatively, a ZZ scaffold segment can be incorporated into an antigen-binding protein to function only as an Fc-binding domain. For example, in one such embodiment, a ZZ scaffold and an antigen-specific peptide, such as AHNP, can be linked to separate portions of an LZ scaffold, to produce a multifunctional antigen-binding protein. Such an embodiment can have an amino acid sequence the same as, or substantially similar to, SEQ ID NO. 9. Similarly, a ZZ scaffold can be linked to an antibody fragment to function as an Fc-binding domain. For example, a ZZ scaffold could be linked to an antibody-derived fragment single chain Fv (scFv) to allow the ScFv to interact with the Fc portion of an antibody. One such embodiment can have an amino acid sequence the same as, or substantially similar to, SEQ ID NO. 10. In some embodiments, the ability of the antigen-binding protein to interact with antibodies may allow for indirect interaction with Fc receptors via the constant region of the antibody. Alternative embodiments of the antigen-binding proteins described in this paragraph can be produced using any of the antigen-specific peptides described in SEQ ID NOs. 13-24.

Also described herein are scaffolds for making antigen-binding proteins that can not only bind to a particular antigen, but can also bind to, or interact with, lymphocytes. Such antigen-binding proteins can have at least one protein segment that is capable of binding to, or interacting with, a lymphocyte surface protein. In some embodiments, the surface protein binding segment can also serve as a scaffold for an antigen-specific peptide. An antigen-binding protein of this sort can be produced by the combination of a protein scaffold derived from a portion of glucocorticoid-induced tumor necrosis factor receptor ligand (GITRL) with an antigen-specific peptide. In one embodiment, this type of antigen-binding protein includes a murine GITRL-based scaffold (SEQ ID NO: 4), derived from a portion of murine GITRL, linked to AHNP. An additional embodiment of this protein, or an analogous antigen-binding protein specific for a different antigen, can also include a detectable label such as an epitope tag, a fluorophore, a radio isotope, or an enzyme (SEQ ID NO. 8). Alternatively, a GITRL scaffold segment can be incorporated into an antigen-binding protein to function as a cellular interaction domain. For example, in one such embodiment, a GITRL scaffold and an antigen-specific peptide, such as AHNP, can be linked to separate portions of a different protein scaffold, to produce a bi-specific antigen-binding protein. Similarly, a GITRL scaffold can be linked to an antibody fragment to function as cellular interaction domain. For example, a murine GITRL scaffold could be linked to a scFv to provide a means to interact with a glucocorticoid-induced tumor necrosis factor receptor expressed on the surface of a cell. One such embodiment can have an amino acid sequence the same as, or substantially similar to, SEQ ID NO. 11. It will be apparent to those of skill in the art that alternative embodiments of such antigen-binding proteins can be produced using any of the antigen-specific peptides described in SEQ ID NOs. 13-24.

Disclosed herein are the amino acid sequences for a number of the scaffolds and antigen-binding proteins described, as such, corresponding nucleotide sequences encoding these described scaffolds and antigen-binding proteins will be apparent to one of skill in the art. Vectors used to express these polynucleotide sequences encoding the disclosed amino acid sequences are also provided. For example, a vector having a polynucleotide sequence encoding an amino acid sequence the same as, or similar to, that of SEQ ID NO. 5. Similarly, a vector having a polynucleotide sequence encoding an amino acid sequence the same as, or similar to, that of SEQ ID NO. 8. A vector having a polynucleotide sequence encoding an amino acid sequence the same as, or similar to, that of SEQ ID NO. 6. Another example includes a vector having a polynucleotide sequence encoding an amino acid sequence that is the same as, or similar to, SEQ ID NO. 7. Another embodiment of a described vector is one that has a polynucleotide sequence encoding an amino acid sequence the same as, or similar to, that of SEQ ID NO. 9. Another embodiment of a described vector is one that has a polynucleotide sequence encoding an amino acid the same as, or similar to, that of SEQ ID NO. 8. Another embodiment of a described vector is one that has a polynucleotide sequence encoding an amino acid sequence the same as, or similar to, that of SEQ ID NO. 3. Another embodiment of a described vector is one that has a polynucleotide sequence encoding an amino acid sequence the same as, or similar to, that of SEQ ID NO. 1. Another embodiment of a described vector is one that has a polynucleotide sequence encoding an amino acid the same as, or similar to, that of SEQ ID NO. 4. For the sake of brevity, only a limited number of vectors having the described polynucleotide sequences are provided; however, alternative vector and polynucleotide combinations for expressing the disclosed antigen-binding proteins will be apparent to those with sufficient skill in the art to understand the degeneracy of the genetic code. Additionally, it is fully contemplated that the disclosed vectors can be used to transform prokaryotic and/or eukaryotic cells to facilitate expression of the described antigen-binding proteins. In some embodiments the described vectors are used to facilitate protein expression in bacteria, such as *E. coli*. While any *E. coli* strain can be used to express the proteins described herein, some preferred strains include: BL21 (DE3), BL21-CodonPlus® (DE3)-RP, BL21-CodonPlus® (DE3)-RIL, BL21-(DE3)-pLysS (Stratagene). Eukaryotic cells can also be used with the described vectors to facilitate protein expression. While those of skill in the art will recognize that a wide variety of eukaryotic cells will be suitable for this purpose, some preferred embodiments include mammalian cells and insect cells. For example, in one embodiment Chinese hamster ovary (CHO) cells can be used with the described vectors to facilitate expression of the protein constructs provided herein. In alternative embodiments, insect cells, such as Sf9 cells or S2 cells, can be used to with the described vectors to facilitate expression of the protein constructs provided herein. Furthermore, those of skill in the art will understand that alternative vectors, not expressly disclosed herein, can be used for the same purpose of expressing, or replicating nucleic acids encoding, the described antigen-binding proteins.

Also described herein are compositions containing an antigen-binding protein and a pharmaceutically acceptable carrier. Such compositions can be used to administer the described antigen-binding proteins to a subject or store or to maintain the described antigen-binding proteins. Any of the described antigen-binding proteins can be used to produce such compositions, which may include more than one of the disclosed antigen-binding proteins. In addition, such compositions can include other agents, such as therapeutic agents, preservatives, antimicrobial agents, and the like.

Methods of using the described scaffolds, or antigen-binding proteins, are also provided. For example, antigen-binding proteins derived from the scaffolds disclosed herein may be used to treat or prevent disease in a subject. The described methods of treating or preventing disease can be used to administer compositions, having antigen-binding proteins derived from the described scaffolds, to a subject in need of such treatment. Also disclosed are methods for detecting an antigen of interest using antigen-binding proteins derived from the scaffolds disclosed herein. Such methods are applicable to antigen detection in a subject, in a sample obtained from a subject, or in vitro.

DETAILED DESCRIPTION OF ILLUSTRATIVE EMBODIMENTS

Figure 1A:
FIGS. 1(a) and 1(b) provide schematic renderings of the scaffolds and antigen binding proteins (or SAbS) described herein.
Figure 1A:
Figure 1A:
Figure 1A:
Figure 1A:
Figure 1A:
Figure 1A:
Figure 1A:

Various terms relating to aspects of the description are used throughout the specification and claims. Such terms are to be given their ordinary meaning in the art unless otherwise indicated. Other specifically defined terms are to be construed in a manner consistent with the definitions provided herein.

As used in this specification and the appended claims, the singular forms "a," "an," and "the" include plural referents unless the content clearly dictates otherwise. Thus, for example, reference to "a cell" includes a combination of two or more cells, and the like.

As used herein, the term "cytotoxic" or "cytostatic" agent refers to an agent that inhibits the biological processes of a cell, or reduces the viability or proliferative potential of a cell. Cytotoxic or cytostatic agents can function in a variety of ways, for example, but not by way of limitation, by inducing DNA damage, inducing cell cycle arrest, inhibiting DNA synthesis, inhibiting transcription, inhibiting translation or protein synthesis, inhibiting cell division, or inducing apoptosis. As used herein, the term "chemotherapeutic agent" refers to cytotoxic, cytostatic, and antineoplastic agents that preferentially kill, inhibit the growth of, or inhibit the metastasis of neoplastic cells or disrupt the cell cycle of rapidly proliferating cells. Chemotherapeutic agents include, but are not limited to, synthetic compounds, natural and recombinant bacterial toxins, natural and recombinant fungal toxins, natural and recombinant plant toxins, fissionable nuclides, and radionuclides. Specific examples of chemotherapeutic agents include, but are not limited to, pokeweed antiviral protein, abrin, ricin and each of their A chains, momordin, saporin, bryodin 1, bouganin, gelonin, Diphtheria toxin, *Pseudomonas* exotoxin, Shiga toxin, calicheamicin, maytansinoid, lead-212, bismuth-212, astatine-211, iodine-131, scandium-47, rhenium-186, rhenium-188, yttrium-90, iodine-123, iodine-124, iodine-125, bromine-77, indium-111, boron-10, actinide, altretamine, actinomycin D, plicamycin, puromycin, gramicidin D, doxorubicin, colchicine, cytochalasin B, cyclophosphamide, emetine, maytansine, amsacrine, cisplastin, etoposide, etoposide orthoquinone, teniposide, daunorubicin, gemcitabine, doxorubicin, mitoxantraone, bisanthrene, Bleomycin, methotrexate, vindesine, adriamycin, vincristine, vinblastine, BCNU, taxol, tarceva, avastin, mitomycin, 5-fluorouracil, cyclophosphamide and certain cytokines such as TNF-alpha and TNF-beta.

"Polynucleotide," synonymously referred to as "nucleic acid molecule" or "nucleic acids," refers to any polyribonucleotide or polydeoxyribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications can be made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short nucleic acid chains, often referred to as oligonucleotides.

"Substantially the same" with respect to nucleic acid or amino acid sequences, means at least about 65% identity between two or more sequences. Preferably, the term refers to at least about 70% identity between two or more sequences, more preferably at least about 75% identity, more preferably at least about 80% identity, more preferably at least about 85% identity, more preferably at least about 90% identity, more preferably at least about 91% identity, more preferably at least about 92% identity, more preferably at least about 93% identity, more preferably at least about 94% identity, more preferably at least about 95% identity, more preferably at least about 96% identity, more preferably at least about 97% identity, more preferably at least about 98% identity, and more preferably at least about 99% or greater identity. Such identity can be determined using mBLAST algorithm (Altschul et al. (1990) Proc. Natl. Acad. Sci. USA 87:2264-8; Karlin and Altschul (1993) Proc. Natl. Acad. Sci. USA 90:5873-7).

A "vector" is a replicon, such as plasmid, phage, cosmid, or virus in which another nucleic acid segment may be operably inserted so as to bring about the replication or expression of the segment.

The term "operably linked" or "operably inserted" means that the regulatory sequences necessary for expression of the coding sequence are placed in a nucleic acid molecule in the appropriate positions relative to the coding sequence so as to enable expression of the coding sequence. By way of example, a promoter is operably linked with a coding sequence when the promoter is capable of controlling the transcription or expression of that coding sequence. Coding sequences can be operably linked to promoters or regulatory sequences in a sense or antisense orientation. The term "operably linked" is sometimes applied to the arrangement of other transcription control elements (e.g., enhancers) in an expression vector.

A cell has been "transformed" or "transfected" by exogenous or heterologous nucleic acids such as DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell, or "stable cell" is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

"Biomolecules" include proteins, polypeptides, nucleic acids, lipids, monosaccharides, polysaccharides, and all fragments, analogs, homologs, conjugates, and derivatives thereof.

The terms "express" and "produce" are used synonymously herein, and refer to the biosynthesis of a gene product. These terms encompass the transcription of a gene into RNA. These terms also encompass translation of RNA into one or more polypeptides, and further encompass all naturally occurring post-transcriptional and post-translational modifications. The expression/production of an antibody or antigen-binding fragment can be within the cytoplasm of the cell, and/or into the extracellular milieu such as the growth medium of a cell culture.

The terms "treating" or "treatment" refer to any success or indicia of success in the attenuation or amelioration of an injury, pathology or condition, including any objective or subjective parameter such as abatement, remission, diminishing of symptoms or making the injury, pathology, or condition more tolerable to the patient, slowing in the rate of degeneration or decline, making the final point of degeneration less debilitating, improving a subject's physical or mental well-being, or prolonging the length of survival. The treatment or amelioration of symptoms can be based on objective or subjective parameters; including the results of a physical examination, neurological examination, and/or psychiatric evaluations.

"Effective amount" and "therapeutically effective amount" are used interchangeably herein, and refer to an amount of an antibody, antigen-binding fragment, or antibody composition, as described herein, effective to achieve a particular biological or therapeutic result such as, but not limited to, biological or therapeutic results disclosed, described, or exemplified herein. A therapeutically effective amount of the antibody or antigen-binding fragment thereof may vary according to factors such as the disease state, age, sex, and weight of the individual, and the ability of the antibody or antigen-binding fragment thereof to elicit a desired response in the individual. Such results may include, but are not limited to, the treatment of cancer, as determined by any means suitable in the art.

"Pharmaceutically acceptable" refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability. "Pharmaceutically acceptable carrier" refers to a medium that does not interfere with the effectiveness of the biological activity of the active ingredient(s) and is not toxic to the host to which it is administered.

"Antibody" refers to all isotypes of immunoglobulins (IgG, IgA, IgE, IgM, IgD, and IgY) including various monomeric and polymeric forms of each isotype, unless otherwise specified.

"Antibody fragments" comprise a portion of a full length antibody, generally the antigen binding or variable region thereof, such as Fab, Fab', F(ab') 2, and Fv fragments; diabodies; linear antibodies; single-chain antibody molecules; and multispecific antibodies formed from antibody fragments. Various techniques have been developed for the production of antibody fragments, including proteolytic digestion of antibodies and recombinant production in host cells; however, other techniques for the production of antibody fragments will be apparent to the skilled practitioner. In some embodiments, the antibody fragment of choice is a single chain Fv fragment (scFv). "Single-chain Fv" or "scFv" antibody fragments comprise the V H and V L domains of antibody, wherein these domains are present in a single polypeptide chain. Generally, the Fv polypeptide further comprises a polypeptide linker between the V H and V L domains which enables the scFv to form the desired structure for antigen binding. For a review of scFv and other antibody fragments, see James D. Marks, Antibody Engineering, Chapter 2, Oxford University Press (1995) (Carl K. Borrebaeck, Ed.).

"Scaffold" refers to a recombinant polypeptide structure that can provide a framework to which another protein or polypeptide may be linked, or fused, to allow for increased stability of the protein or peptide or to place the protein or peptide in a more preferred conformation, or form, to mediate a desired biological activity.

"Link" in the context of a scaffold or antigen-binding protein means "connected to" either directly or indirectly.

Indirect linkage can be mediated by a polypeptide linker such as poly-glycine or a glycine-serine polypeptide, for example, GGGGS (SEQ ID NO: 25) or GGGGGS (SEQ ID NO: 26). Other such linkers are known in the art and should be considered to be encompassed by this term.

The novel protein scaffolds described herein have been designed to provide a framework on which one or more antigen specific peptides may be placed to produce an antigen-binding protein. In some instances, however, having a protein that can bind to an antigen and also accomplish some alternative function is also desired. Therefore, also disclosed herein are proteins that can not only serve as a scaffold, but also can provide one or more alternative functions, such as binding to a non-antigen protein of interest.

One aspect of the described scaffold proteins is the ability to provide a framework that will allow one or more antigen-specific peptides to assume a conformation that will cause the peptide to bind an antigen. One desirable aspect of an antigen-binding protein is that it multimerize. Multimeric units will likely have more functional antigen-binding sites available, which can increase the avidity and overall propensity of the antigen-binding protein to bind to its antigen. In this regard, crystallographic studies of the FOXP3 protein indicated that the leucine zipper domain of the protein forms dimeric units, which, once formed can dimerize with other dimers to form tetramers. As described in the examples, and shown in the figures, a FOXP3-based scaffold was able to form an antigen-binding protein when linked to AHNP. Accordingly, in one embodiment, a scaffold protein can have an amino acid sequence of, or substantially similar to, (SEQ ID NO. 1). A further embodiment of this type of scaffold protein can occur in the form of an antigen-binding protein, one embodiment of which is represented by a scaffold protein having an amino acid sequence of, or substantially similar to, (SEQ ID NO. 5). The antigen-binding proteins exemplified herein have been made with the antigen-specific peptide AHNP, which allows for comparative studies between the scaffolds, and antibodies or antibody fragments that include this peptide. This practical aspect of the present disclosure should not be considered to limit the scaffolds provided herein for use with only AHNP, as it should be apparent that these scaffolds can be used with a wide variety of antigen-specific peptides. While the particular amino acid sequences provided represent the specific embodiments exemplified herein, it should be understood that certain amino acid substitutions, deletions, or additions could be made to the described sequences that would not alter the function of the described scaffolds or antigen-binding proteins. Therefore, it is contemplated that scaffolds or antigen-binding proteins having at least 80% homology to those described herein are within the scope of the disclosed subject matter. Furthermore, it is contemplated that scaffolds or antigen-binding proteins having at least 85% homology to those described herein are within the scope of the disclosed subject matter. In addition, it is contemplated that scaffolds or antigen-binding proteins having at least 90% homology to those described herein are within the scope of the disclosed subject matter. Moreover, it is contemplated that scaffolds or antigen-binding proteins having at least 95% homology to those described herein are within the scope of the disclosed subject matter.

Also disclosed herein are proteins that can serve as multifunctional scaffolds. Multifunctional scaffolds cannot only serve as scaffolds for one or more antigen-specific peptides, they can also carry out one or more alternative functions, such as binding to a non-antigenic protein. Scaffolds of this sort have two basic features: 1) the ability to provide a framework the maintains, enhances, or allows the ability of an antigen-specific peptide to bind to its antigen, and 2) the ability to carry out at least one separate biological function, such as binding to another, non-antigen, protein. For example, a multifunctional scaffold could have the ability to bind to a cellular receptor, in addition to providing a structural framework for an antigen-specific peptide. An antigen-binding protein incorporating such a scaffold would have the ability to not only bind the antigen corresponding to the antigen-specific peptide, but would also have the ability to interact with a receptor on a cell surface.

Several multifunctional scaffold proteins are disclosed herein. For example, a multifunctional scaffold can be composed from, or incorporate, a protein segment designed to mimic the CH2 domain of an immunoglobulin heavy chain. One embodiment of this sort of scaffold is exemplified by an amino acid sequence of, or substantially similar to, (SEQ ID NO. 2). Another embodiment of a multifunctional scaffold can be composed from, or incorporate, a portion of Protein A, which, in addition to acting as a scaffold, could also allow for binding to the Fc portion of an antibody. One example of this type of scaffold is embodied by an amino acid sequence of, or substantially similar to, (SEQ ID NO. 3). Moreover, a multifunctional scaffold can be composed from, or incorporate, a portion of the GITRL protein. In addition to binding antigen, an antigen-binding protein having a GITRL segment would have the ability to interact with cells, such as T cells, that display the receptor for GITRL. One example of such a scaffold is embodied by an amino acid sequence of, or substantially similar to, (SEQ ID NO. 4). While the particular amino acid sequences provided represent the specific embodiments exemplified herein, it should be understood that certain amino acid substitutions, deletions, or additions could be made to the described sequences that would not alter the function of the described scaffolds or antigen-binding proteins. Therefore, it is contemplated that scaffolds or antigen-binding proteins having at least 80% homology to those described herein are within the scope of the disclosed subject matter. Furthermore, it is contemplated that scaffolds or antigen-binding proteins having at least 85% homology to those described herein are within the scope of the disclosed subject matter. In addition, it is contemplated that scaffolds or antigen-binding proteins having at least 90% homology to those described herein are within the scope of the disclosed subject matter. Moreover, it is contemplated that scaffolds or antigen-binding proteins having at least 95% homology to those described herein are within the scope of the disclosed subject matter.

Multifunctional scaffolds, such as those described herein, can be used to make antigen-binding proteins, which can take a variety of forms. For example, a multifunctional scaffold could be linked or combined with one or more antigen-specific peptide to form an antigen-binding protein with the ability to bind to an antigen and a cellular protein. In addition, a multifunctional antigen-binding protein can be produced by combining two or more multifunctional scaffolds, where an antigen-specific peptide has been incorporated to at least one such multifunctional scaffold. Furthermore, a multifunctional antigen-binding protein can be produced by combining two or more multifunctional scaffolds, each of which incorporate the same antigen-specific peptide. As will be apparent to those of skill in the art, numerous possible combinations exist by which one could produce a multifunctional antigen-binding protein using one or more multifunctional scaffolds, and while each possibility is not expressly described herein, for the sake of brevity, such scaffold combinations and antigen-binding proteins are considered to fall within the scope of this disclosure.

Several multifunctional antigen-binding proteins are disclosed herein. For example, a multifunctional antigen-binding protein can be composed by linking a protein designed to mimic a portion of the CH2 domain of an immunoglobulin heavy chain with an antigen-specific peptide, such as AHNP. One embodiment of this sort of antigen-binding protein is exemplified by an amino acid sequence of, or substantially similar to, (SEQ ID NO. 6). Another embodiment of a multifunctional antigen-binding protein can be composed by linking a portion of Protein A to an antigen-specific peptide, such as AHNP. One example of this type of scaffold is embodied by an amino acid sequence of, or substantially similar to, (SEQ ID NO. 7). Moreover, a multifunctional antigen-binding protein can be composed by linking a portion of the GITRL protein with an antigen-specific peptide, such as AHNP. One example of this type of antigen-binding protein is embodied by an amino acid sequence of, or substantially similar to, (SEQ ID NO. 8). The antigen-binding proteins exemplified herein have been made with the antigen-specific peptide AHNP, which allows for comparative studies between the scaffolds, and antibodies or antibody fragments that include this peptide. This practical aspect of the present disclosure should not be considered to limit the disclosed scaffolds to use with only AHNP, as it should be apparent that these scaffolds can be used with a wide variety of antigen-specific peptides. Furthermore, while the particular amino acid sequences provided represent the specific embodiments exemplified herein, it should be understood that certain amino acid substitutions, deletions, or additions could be made to the described sequences that would not alter the function of the described scaffolds or antigen-binding proteins. Therefore, it is contemplated that scaffolds or antigen-binding proteins having at least 80% homology to those described herein are within the scope of the disclosed subject matter. Furthermore, it is contemplated that scaffolds or antigen-binding proteins having at least 85% homology to those described herein are within the scope of the disclosed subject matter. In addition, it is contemplated that scaffolds or antigen-binding proteins having at least 90% homology to those described herein are within the scope of the disclosed subject matter. Moreover, it is contemplated that scaffolds or antigen-binding proteins having at least 95% homology to those described herein are within the scope of the disclosed subject matter.

Multifunctional antigen-binding proteins can be produced by combining at least one multifunctional scaffold with another scaffold, where at least one scaffold is linked to an antigen-specific peptide. For example, the ZZ scaffold could be fused or linked to an existing antigen-binding protein, such as ALZ, to form a new, multifunctional antigen-binding protein. One embodiment of such an antigen-binding protein is exemplified by SEQ ID NO. 9. A multifunctional antigen-binding protein can also be produced by linking a multifunctional scaffold to an antigen-specific antibody or antibody fragment, such as an Fab or scFv. In this instance, the scaffold portion, may or may not also be linked to an antigen-specific peptide. One example of a scaffold-linked scFv is provided herein by linking the 4D5-scFv with the ZZ scaffold, which can be embodied by an amino acid sequence of, or substantially similar to, (SEQ ID NO. 10). Another example of a scaffold-linked scFv is provided herein by linking the 4D5-scFv with the murine GITRL scaffold, which can be embodied by an amino acid sequence of, or substantially similar to, (SEQ ID NO. 11). The antigen-binding proteins exemplified herein have been made with an scFv specific for the Her2/neu protein, which allows for comparative studies between the scaffolds, and antibodies or antibody fragments that include AHNP. This practical aspect of the present disclosure should not be considered to limit the disclosed scaffolds for use with only scFv proteins specific for the Her2/neu protein, as it should be apparent that these scaffolds can be used with a wide variety of scFv proteins or other antibody fragments, such as those specific for EGFR Furthermore, while the particular amino acid sequences provided represent the specific embodiments exemplified herein, it should be understood that certain amino acid substitutions, deletions, or additions could be made to the described sequences that would not alter the function of the described scaffolds or antigen-binding proteins. Therefore, it is contemplated that scaffolds or antigen-binding proteins having at least 80% homology to those described herein are within the scope of the disclosed subject matter. Furthermore, it is contemplated that scaffolds or antigen-binding proteins having at least 85% homology to those described herein are within the scope of the disclosed subject matter. In addition, it is contemplated that scaffolds or antigen-binding proteins having at least 90% homology to those described herein are within the scope of the disclosed subject matter. Moreover, it is contemplated that scaffolds or antigen-binding proteins having at least 95% homology to those described herein are within the scope of the disclosed subject matter.

The antigen-binding proteins described herein can be labeled or otherwise conjugated to various chemical or biomolecule moieties, for example, for therapeutic or diagnostic applications. The moieties can be cytotoxic, for example, bacterial toxins, viral toxins, radioisotopes, and the like. The moieties can be detectable labels, for example, fluorescent labels, radiolabels, biotin, protein tags and the like, for example a poly-histidine tag. In addition, solublizing factors, such as Trx can be appended or linked to the scaffolds or antigen binding proteins disclosed herein (e.g., SEQ ID NO. 6).

The described antigen-binding proteins are primarily composed of smaller components linked together, either directly or indirectly. For example, a protein scaffold can be indirectly linked to an antigen-specific peptide or multifunctional protein scaffold (or both) via a polypeptide linker, such as polyglycine or glycine-serine linker. Particular embodiments of glycine-serine linkers are provided herein as GGGGS (SEQ ID NO. 25) or GGGGGS (SEQ ID NO. 26) and are exemplified in the amino acid sequences of the various antigen-binding proteins provided. Of course, other linkers are well known in the art and are considered within the scope of the subject matter provided herein. (Robinson and Sauer, 95 PNAS 5929-34 (1998), Tang et al., 271(26) J. Bio. Chem. 15682-86 (1996). In addition, the various components of the antigen-binding proteins described herein can be directly linked to one another by splicing together their respective gene segments via genetic engineering techniques well known in the art.

TABLE 1

Exemplary amino acid sequences of scaffolds and antigen-binding proteins.

| SEQ ID NO. | Protein | Exemplary Amino Acid Sequence |
|---|---|---|
| 1 | LZ domain | MASDFLKHCQADHLLDEKGRAQCLLQREMVQSLE QQLVLEKEKLSAMQAHLAGKMALTKASSVASSDK |
| 2 | CH2 mimic | FPAPLAPGGLYLGG |
| 3 | ZZ domain | VDNKFNKEQQNAFYEILHLPNLNEEQRNAFIQSLKD DPSQSANLLAEAKKLNDAQAPK |
| 4 | GITRL domain | QLETAKEPCMAKFGPLPSKWQMASSEPPCVNKVSD WKLEILQNGLYLIYGQVAPNANYNDVAPFEVRLYK NKDMIQTLTNKSKIQNVGGTYELHVGDTIDLIFNSE HQVLKNNTYWGIILLANPQFIS |
| 5 | ALZ | MAFCDGFYACYMDVGGGGGSMASDFLKHCQADH LLDEKGRAQCLLQREMVQSLEQQLVLEKEKLSAM QAHLAGKMALTKASSVASSDKLEHHHHHH |
| 6 | AHNP-CH2 mimic | MAFCDGFYACYMDVGGGGGSFPAPLAPGGLYLGG ENLYFQGMSDKIIHLTDDSFDTDVLKADGAILVDF WAEWCGPCKMIAPILDEIADEYQGKLTVAKLNIDQ NPGTAPKYGIRGIPTLLLFKNGEVAATKVGALSKGQ LKEFLDANLALEHHHHHH |
| 7 | AZZ | MAFCDGFYACYMDVGGGGGSVDNKFNKEQQNAF YEILHLPNLNEEQRNAFIQSLKDDPSQSANLLAEAK KLNDAQAPKLEHHHHHH |
| 8 | AGITRL | MAFCDGFYACYMDVGGGGGSQLETAKEPCMAKF GPLPSKWQMASSEPPCVNKVSDWKLEILQNGLYLI YGQVAPNANYNDVAPFEVRLYKNKDMIQTLTNKS KIQNVGGTYELHVGDTIDLIFNSEHQVLKNNTYWGI ILLANPQFISLEHHHHHH |
| 9 | ALZ-ZZ | MAFCDGFYACYMDVGGGGGSMASDFLKHCQADH LLDEKGRAQCLLQREMVQSLEQQLVLEKEKLSAM QAHLAGKMALTKASSVASSDKGGGGSELVDNKFN KEQQNAFYEILHLPNLNEEQRNAFIQSLKDDPSQSA NLLAEAKKLNDAQAPKLEHHHHHH |
| 10 | 4D5 scFv-ZZ | MADIQMTQSPSSLSASVGDRVTITCRASQDVNTAV AWYQQKPGKAPKLLIYSASFLYSGVPSRFSGSGSGT DFTLTISSLQPEDFATYYCQQHYTTPPTFGQGTKVE LKRATPSHNSHQVPSAGGPTANSGEVKLVESGGGL VQPGGSLRLSCATSGFNIKDTYIHWVRQAPGKGLE WVARIYPTNGYTRYADSVKGRFTISADTSKNTAYL QMNSLRAEDTAVYYCSRWGGDGFYAMDYWGQGT TVTVSSGGGGSVDNKFNKEQQNAFYEILHLPNLNE EQRNAFIQSLKDDPSQSANLLAEAKKLNDAQAPKL EHHHHHH |
| 11 | 4D5 scFv-GITRL | MADIQMTQSPSSLSASVGDRVTITCRASQDVNTAV AWYQQKPGKAPKLLIYSASFLYSGVPSRFSGSRSGT DFTLTISSLQPEDFATYYCQQHYTTPPTFGQGTKVE LKRATPSHNSHQVPSAGGPTANSGEVKLVESGGGL VQPGGSLRLSCATSGFNIKDTYIHWVRQAPGKGLE WVARIYPTNGYTRYADSVKGRFTISADTSKNTAYL QMNSLRAEDTAVYYCSRWGGDGFYAMDYWGQGT TVTVSSGGGGSQLETAKEPCMAKFGPLPSKWQMAS SEPPCVNKVSDWKLEILQNGLYLIYGQVAPNANYN DVAPFEVRLYKNKDMIQTLTNKSKIQNVGGTYELH VGDTIDLIFNSEHQVLKNNTYWGIILLANPQFISLEH HHHHH |
| 12 | AHNP | FCDGFYACYMDV |
| 13 | AHNPY | YCDGFYACYMDV |
| 14 | B2BPT | YCFPDEEGACY |
| 15 | B2BPT | PCPINCTHSCVDLDDKGCPAEQRASPLTSI |
| 16 | B2APE | YCPIWKFPDEECY |
| 17 | S22 | YCFPDEEGACY |

TABLE 1-continued

Exemplary amino acid sequences of scaffolds and antigen-binding proteins.

| SEQ ID NO. | Protein | Exemplary Amino Acid Sequence |
|---|---|---|
| 18 | EP1 | YCGYSSTSYCFVMD |
| 19 | EP2 | YCASRDYDYDGRCYFD |
| 20 | EP3 | YCTRGYSSTSYCYAMD |
| 21 | EP4 | FCMEESGGNYCY |
| 22 | EP5 | YCALRGGVYWPCY |
| 23 | EP6 | YCALTYYDYECFAY |
| 24 | B1ALG | YCLVWKYADAGCY |

The scaffolds and antigen-binding proteins described herein can be made by recombinant processes and, therefore, may include amino acid sequences derived from more than one species (i.e. chimeric constructs) or may be engineered to have a human, or human-like, amino acid composition (i.e., a humanized construct). Accordingly, provided herein are vectors comprising polynucleotides capable of encoding the described scaffolds and antigen-binding proteins. The vectors can be expression vectors. Recombinant expression vectors containing a sequence encoding a polypeptide of interest are thus provided. The expression vector may contain one or more additional sequences such as, but not limited to, regulatory sequences (e.g., promoter, enhancer), a selection marker, and a polyadenylation signal. Vectors for transforming a wide variety of host cells are well known to those of skill in the art. They include, but are not limited to, plasmids, phagemids, cosmids, baculoviruses, bacmids, bacterial artificial chromosomes (BACs), yeast artificial chromosomes (YACs), as well as other bacterial, yeast and viral vectors. The vectors described herein may be integrated into the host genome or maintained independently in the cell or nucleus.

Recombinant expression vectors contemplated to be within the scope of the description include synthetic, genomic, or cDNA-derived nucleic acid fragments that encode at least one recombinant protein which may be operably linked to suitable regulatory elements. Such regulatory elements may include a transcriptional promoter, sequences encoding suitable mRNA ribosomal binding sites, and sequences that control the termination of transcription and translation. Expression vectors, especially mammalian expression vectors, may also include one or more nontranscribed elements such as an origin of replication, a suitable promoter and enhancer linked to the gene to be expressed, other 5' or 3' flanking nontranscribed sequences, 5' or 3' nontranslated sequences (such as necessary ribosome binding sites), a polyadenylation site, splice donor and acceptor sites, or transcriptional termination sequences. An origin of replication that confers the ability to replicate in a host may also be incorporated. Such vectors may be integrated into the host genome or maintained independently in the cell or nucleus.

The vectors described herein can be used to transform various cells with the genes encoding the disclosed scaffolds or antigen-binding proteins. For example, the vectors may be used to generate scaffold or antigen-binding protein-producing cells or cell lines. Thus, another aspect features host cells transformed with vectors comprising a nucleic acid sequence encoding a scaffold or antigen-binding protein, such as the scaffolds or antigen-binding proteins disclosed and exemplified herein. The host cells disclosed herein can be prokaryotic or eukaryotic cells, For example the host cell can be a bacteria. In a preferred embodiment, the bacterial host cell is E. coli. Of course, the host cell can also be a mammalian cell, such as a Chinese hamster ovary (CHO) cell line. Numerous other such host cells, prokaryotic and eukaryotic, are known in the art and are considered to be within the scope of this disclosure.

Numerous techniques are known in the art for the introduction of foreign genes into cells and may be used to construct the recombinant cells for purposes of carrying out the inventive methods, in accordance with the various embodiments described and exemplified herein. The technique used should provide for the stable transfer of the heterologous gene sequence to the host cell, such that the heterologous gene sequence is heritable and expressible by the cell progeny, and so that the necessary development and physiological functions of the recipient cells are not disrupted. Techniques which may be used include but are not limited to chromosome transfer (e.g., cell fusion, chromosome mediated gene transfer, micro cell mediated gene transfer), physical methods (e.g., transfection, spheroplast fusion, microinjection, electroporation, liposome carrier), viral vector transfer (e.g., recombinant DNA viruses, recombinant RNA viruses) and the like. Calcium phosphate precipitation and polyethylene glycol (PEG)-induced fusion of bacterial protoplasts with mammalian cells can also be used to transform cells.

Methods of using the described scaffolds, or antigen-binding proteins, are also provided. For example, antigen-binding proteins derived from the scaffolds disclosed herein may be used to treat or prevent disease in a subject. The described methods of treating or preventing disease can be used to administer compositions, having antigen-binding proteins derived from the described scaffolds, to a subject in need of such treatment. Also disclosed are methods for detecting an antigen of interest using antigen-binding proteins derived from the scaffolds disclosed herein. Such methods are applicable to antigen detection in a subject, in a sample obtained from a subject, or in vitro. The methods described herein can be particularly applicable to treating or preventing diseases associated with the Her2/neu receptor, such as administering to the subject one of the antigen-binding proteins disclosed herein and a pharmaceutically acceptable carrier. Methods described herein can also be used to treat or prevent diseases associated with the epidermal growth factor receptor (EGFR), such as administering to the subject one of the EGFR-specific antigen-binding proteins disclosed herein and a pharmaceutically acceptable carrier.

Alternatively, antigen-binding proteins derived from the scaffolds disclosed herein may be used to detect disease-causing agents or disease associated proteins or metabolites in a subject or a sample obtained from a subject, which in turn can allow for a diagnosis. The methods described herein can be particularly applicable to detecting or otherwise assessing the expression of the Her2/neu receptor or EGFR in a subject. For example, one could inject the patient with a detectably labeled embodiment of one of the antigen-binding proteins described herein and detect the localization and/or intensity of the signal in the subject. Alternatively, one could expose a sample containing the Her2/neu receptor or EGFR to the receptor-specific antigen-binding proteins described herein, and detecting binding of said antigen-binding protein to said sample.

In some embodiments, the disclosed antigen-binding proteins are conjugated to one or more chemotherapeutic agents such as, but not limited to radionuclides, toxins, and cytotoxic and cytostatic agents. In other embodiments the antigen-binding proteins are used in combination with one or more chemotherapeutic agents. The antigen-binding proteins described herein may be used alone or with (e.g., coadministered or conjugated to) a biomolecule or chemotherapeutic agent such as a cytotoxic or cytostatic agent. In some embodiments, the chemotherapeutic agent is a radionuclide, including, but not limited to lead-212, bismuth-212, astatine-211, iodine-131, scandium-47, rhenium-186, rhenium-188, yttrium-90, iodine-123, iodine-124, iodine-125, bromine-77, indium-111, and fissionable nuclides such as boron-10 or an actinide. In other embodiments, the chemotherapeutic agent is a toxin or cytotoxic drug, pokeweed antiviral protein, abrin, ricin and each of their A chains, momordin, saporin, bryodin 1, bouganin, gelonin, Diphtheria toxin, Pseudomonas exotoxin, Shiga toxin, calicheamicin, maytansinoid, altretamine, actinomycin D, plicamycin, puromycin, gramicidin D, doxorubicin, colchicine, cytochalasin B, cyclophosphamide, emetine, maytansine, amsacrine, cisplastin, etoposide, etoposide orthoquinone, teniposide, daunorubicin, gemcitabine, doxorubicin, mitoxantraone, bisanthrene, Bleomycin, methotrexate, pemetrexed, cisplatinum, vindesine, adriamycin, vincristine, vinblastine, BCNU, taxol, tarceva, avastin, mitomycin, 5-fluorouracil, cyclophosphamide, certain cytokines such as TNF-alpha and TNF-beta, and the like. Methods of conjugation of scaffolds or antigen-binding proteins to such agents are known in the literature.

Described herein are compositions comprising at least one disclosed scaffold or antigen-binding protein and a pharmaceutically acceptable carrier. The compositions can be formulated as any of various preparations that are known and suitable in the art, including those described and exemplified herein. In some embodiments, the compositions are aqueous formulations. Aqueous solutions can be prepared by admixing the antigen-binding proteins in water or suitable physiologic buffer, and optionally adding suitable colorants, flavors, preservatives, stabilizing and thickening agents and the like as desired. Aqueous suspensions can also be made by dispersing the antigen-binding proteins in water or physiologic buffer with viscous material, such as natural or synthetic gums, resins, methylcellulose, sodium carboxymethylcellulose, and other well-known suspending agents.

Also included are liquid formulations and solid form preparations which are intended to be converted, shortly before use, to liquid preparations. Such liquids include solutions, suspensions, syrups, slurries, and emulsions. Liquid preparations may be prepared by conventional means with pharmaceutically acceptable additives such as suspending agents (e.g., sorbitol syrup, cellulose derivatives or hydrogenated edible fats or oils); emulsifying agents (e.g., lecithin or acacia); non-aqueous vehicles (e.g., almond oil, oily esters, or fractionated vegetable oils); and preservatives (e.g., methyl or propyl-p-hydroxybenzoates or sorbic acid). These preparations may contain, in addition to the active agent, colorants, flavors, stabilizers, buffers, artificial and natural sweeteners, dispersants, thickeners, solubilizing agents, and the like. The compositions may be in powder or lyophilized form for constitution with a suitable vehicle such as sterile water, physiological buffer, saline solution, or alcohol, before use.

The compositions can be formulated for injection into a subject. For injection, the compositions described can be formulated in aqueous solutions such as water or alcohol, or in physiologically compatible buffers such as Hanks's solution, Ringer's solution, or physiological saline buffer. The solution may contain formulatory agents such as suspending, stabilizing and/or dispersing agents. Injection formulations may also be prepared as solid form preparations which are intended to be converted, shortly before use, to liquid form preparations suitable for injection, for example, by constitution with a suitable vehicle, such as sterile water, saline solution, or alcohol, before use.

The compositions can be formulated in sustained release vehicles or depot preparations. Such long acting formulations may be administered by implantation (for example subcutaneously or intramuscularly) or by intramuscular injection. Thus, for example, the compositions may be formulated with suitable polymeric or hydrophobic materials (for example, as an emulsion in an acceptable oil) or ion exchange resins, or as sparingly soluble derivatives, for example, as a sparingly soluble salt. Liposomes and emulsions are well-known examples of delivery vehicles suitable for use as carriers for hydrophobic drugs.

The antigen-binding proteins described herein may be administered orally in any acceptable dosage form such as capsules, tablets, aqueous suspensions, solutions or the like. The antigen-binding proteins may also be administered parenterally including but not limited to: subcutaneous, intravenous, intramuscular, intra-articular, intra-synovial, intrasternal, intranasal, topically, intrathecal, intrahepatic, intralesional, and intracranial injection or infusion techniques. Generally, the antigen-binding proteins will be intravenously or intraperitoneally, for example, by injection.

The subject can be any animal, and preferably is a mammal such as a mouse, rat, hamster, guinea pig, rabbit, cat, dog, monkey, donkey, cow, horse, pig, and the like. Most preferably, the mammal is a human. In some embodiments, subjects can be administered at least one antigen-binding protein in a daily dose range of about 0.01 µg to about 500 mg of antigen-binding protein per kg of the weight of the subject. The dose administered to the subject can also be measured in terms of total amount of the at least one antigen-binding protein administered per day. In some embodiments, a subject is administered about 5 to about 5000 milligrams of at least one antigen-binding protein per day. In some embodiments, a subject is administered up to about 10 milligrams of at least one a antigen-binding protein per day. In some embodiments, a subject is administered up to about 100 milligrams of at least antigen-binding protein per day. In some embodiments, a subject is administered up to about 250 milligrams of at least one antigen-binding protein per day. In some embodiments, a subject is administered up to about 500 milligrams of at least one antigen-binding protein per day. In some embodiments, a subject is administered up to about 750 milligrams of at least one antigen-binding protein per day. In some embodiments, a subject is administered up to about 1000 milligrams of at least one antigen-binding protein per day. In some embodiments, a subject is administered up to about 1500 milligrams of at least one antigen-binding protein per day. In some embodiments, a subject is administered up to about 2000 milligrams of at least one antigen-binding protein per day. In some embodiments, a subject is administered up to about 2500 milligrams of at least one antigen-binding protein per day. In some embodiments, a subject is administered up to about 3000 milligrams of at least one antigen-binding protein per day. In some embodiments, a subject is administered up to about 3500 milligrams of at least one antigen-binding protein per day. In some embodiments, a subject is administered up to about 4000 milligrams of at least one antigen-binding protein per day. In some embodiments, a subject is administered up to about 4500 milligrams of at least one antigen-binding protein per day. In some embodiments, a subject is administered up to about 5000 milligrams of at least one antigen-binding protein per day. In some embodiments, the antigen-binding protein is administered to a subject weekly or bi-weekly.

For effective treatment, one skilled in the art may recommend a dosage schedule and dosage amount adequate for the subject being treated. It may be preferred that dosing occur one to four or more times daily for as long as needed. The dosing may occur less frequently if the compositions are formulated in sustained delivery vehicles. The dosage schedule may also vary depending on the active drug concentration, which may depend on the needs of the subject.

There are several embodiments that follow from the description provided above, particularly those relating to antigen-binding proteins and multifunctional antigen-binding proteins. In one embodiment, a multifunctional antigen-binding protein can have at least one multifunctional recombinant protein scaffold and at least one antigen-specific peptide. A further embodiment could be constructed such that the multifunctional antigen-binding protein has at least one multifunctional recombinant protein scaffold linked to an antigen-specific peptide, allowing the antigen-specific protein to bind a protein other that bound by said antigen-specific peptide. In another embodiment, a multifunctional antigen-binding protein is made to have at least one recombinant protein scaffold, at least one multifunctional recombinant protein scaffold, and at least one antigen-specific peptide, where the recombinant protein scaffold is linked to at least one antigen-specific peptide and at least one multifunctional recombinant protein scaffold, such that the multifunctional antigen-binding protein is capable of binding to a protein other that bound by the antigen-specific peptide. The multifunctional antigen-binding proteins described above could be composed from a multifunctional recombinant protein scaffold such as any one, or more, of the multifunctional recombinant protein scaffolds exemplified by the amino acid sequences of SEQ ID NO. 2, SEQ ID NO. 3, or SEQ ID NO. 4. In some embodiments, the multifunctional recombinant protein scaffold will have only the amino acid sequence of SEQ ID NO. 2, SEQ ID NO. 3, or SEQ ID NO. 4, while in other embodiments the multifunctional recombinant protein scaffold can include SEQ ID NO. 2, SEQ ID NO. 3, or SEQ ID NO. 4, in addition to other amino acid sequences. In addition, the described antigen-binding proteins can incorporate any number of antigen-specific peptides, such as the antigen-specific peptide of SEQ ID NO. 12. Furthermore, the described multifunctional antigen-binding proteins can incorporate one or more linkers, made of at least one glycine residue, that connect the components of the protein. In a particular embodiment, the linker described above can have an amino acid sequence of, or similar to, that of SEQ ID NO. 25 or SEQ ID NO. 26. In some embodiments, the linker will have only the amino acid sequence of SEQ ID NO. 25 or SEQ ID NO. 26, while in other embodiments a linker can include SEQ ID NO. 25 or SEQ ID NO. 26 in addition to other amino acid sequences. In one embodiment the multifunctional antigen-binding protein previously described can include a protein domain that promotes solubility. In a preferred embodiment, the protein domain that promotes solubility is Trx. In other embodiments, any of the multifunctional antigen-binding proteins described herein can have an epitope tag, a fluorophore, a radio isotope, or an enzyme. In a preferred embodiment, the embodied multifunctional antigen-binding protein has an epitope tag that is a poly-histidine tag.

The described antigen-binding proteins can be encoded by a variety of polynucleotides capable of encoding the amino acid sequences provided herein. These polynucleotides can also be incorporated into vectors useful for the maintenance, replication, and/or expression of the polynucleotides encoding the described antigen-binding proteins or the described portions thereof. The vectors described above can be used to engineer cells to express the antigen-binding proteins or the described portions thereof encoded by the polynucleotides disclosed herein.

Also provided herein are composition that include the multifunctional antigen-binding proteins described herein and a pharmaceutically acceptable carrier. Such compositions are useful in the methods provided herein for treating or preventing disease in a subject. In one embodiment, the described methods of treatment include administering a therapeutic amount of a one or more of the described multifunctional antigen-binding proteins to a subject in need of such treatment. Similarly, in one embodiment, the described methods of preventing disease in a subject include administering a therapeutic amount of a one or more of the described multifunctional antigen-binding proteins to a subject in need thereof. A preferred method of treating or preventing a disease relate to a disease associated with the Her2/neu receptor or EGFR in a subject, where the treatment or prevention includes administering to the subject a composition including a multifunctional antigen-binding protein described herein. Also provided are methods of detecting an antigen of interest in a subject that include administering a multifunctional antigen-binding protein provided herein to a subject and detecting binding of the multifunctional antigen-binding protein to an antigen of interest. A preferred method of detection involves using at least one of the multifunctional antigen-binding proteins described to detect the Her2/neu receptor by exposing a sample containing the Her2/neu receptor to a multifunctional antigen-binding protein and detecting binding of at least one multifunctional antigen-binding protein to the sample. Another preferred method of detection involves using at least one of the multifunctional antigen-binding proteins described to detect EGFR by exposing a sample containing EGFR to a multifunctional antigen-binding protein and detecting binding of at least one multifunctional antigen-binding protein to the sample.

In addition to the embodiments described above, also disclosed are recombinant protein scaffolds made from a recombinant polypeptide derived from a leucine zipper domain. In one embodiment, the leucine zipper domain of the recombinant protein scaffold is derived from the FOXP3 protein. Such a scaffold can be used to construct an antigen-binding protein having an antigen-specific peptide and optionally having a detectable label. In a preferred embodiment, the recombinant protein scaffold can have an amino acid sequence of, or similar to, SEQ ID NO. 1; the antigen-specific peptide can have an amino acid sequence of, or similar to, SEQ ID NO. 12, and the detectable label is an epitope, a fluorophore, a radio isotope, or an enzyme. In a preferred embodiment, the recombinant antigen-binding protein has an epitope tag that is a poly-histidine tag. Furthermore, the described recombinant antigen-binding proteins can incorporate one or more linkers, made of at least one glycine residue, that connect the components of the protein. In a particular embodiment, the linker described above can have an amino acid sequence of, or similar to, that of SEQ ID NO. 25 or SEQ ID NO. 26. In one embodiment the recombinant antigen-binding protein previously described can include a protein domain that promotes solubility. In a preferred embodiment, the protein domain that promotes solubility is Trx.

The described antigen-binding proteins can be encoded by a variety of polynucleotides capable of encoding the amino acid sequences provided herein. These polynucleotides can also be incorporated into vectors useful for the maintenance, replication, and/or expression of the polynucleotides encoding the described antigen-binding proteins or the described portions thereof. The vectors described above can be used to engineer cells to express the antigen-binding proteins or the described portions thereof encoded by the polynucleotides disclosed herein.

Also provided herein are compositions that include the antigen-binding proteins described herein and a pharmaceutically acceptable carrier. Such compositions are useful in the methods provided herein for treating or preventing disease in a subject. In one embodiment, the described methods of treatment include administering a therapeutic amount of a one or more of the described antigen-binding proteins to a subject in need of such treatment. Similarly, in one embodiment, the described methods of preventing disease in a subject include administering a therapeutic amount of a one or more of the described antigen-binding proteins to a subject in need thereof. A preferred method of treating or preventing a disease relate to a disease associated with the Her2/neu receptor or EGFR in a subject, where the treatment or prevention includes administering to the subject a composition including a antigen-binding protein described herein. Also provided are methods of detecting an antigen of interest in a subject that include administering a antigen-binding protein provided herein to a subject and detecting binding of the antigen-binding protein to an antigen of interest. A preferred method of detection involves using at least one of the antigen-binding proteins described to detect the either the Her2/neu receptor or EGFR by exposing a sample containing either receptor to an antigen-binding protein and detecting binding of at least one antigen-binding protein to the sample.

The following examples are provided to describe the embodiments described herein with greater detail. They are intended to illustrate, not to limit, the embodiments.

EXAMPLE 1

Production of SAbS

Figure 1B:
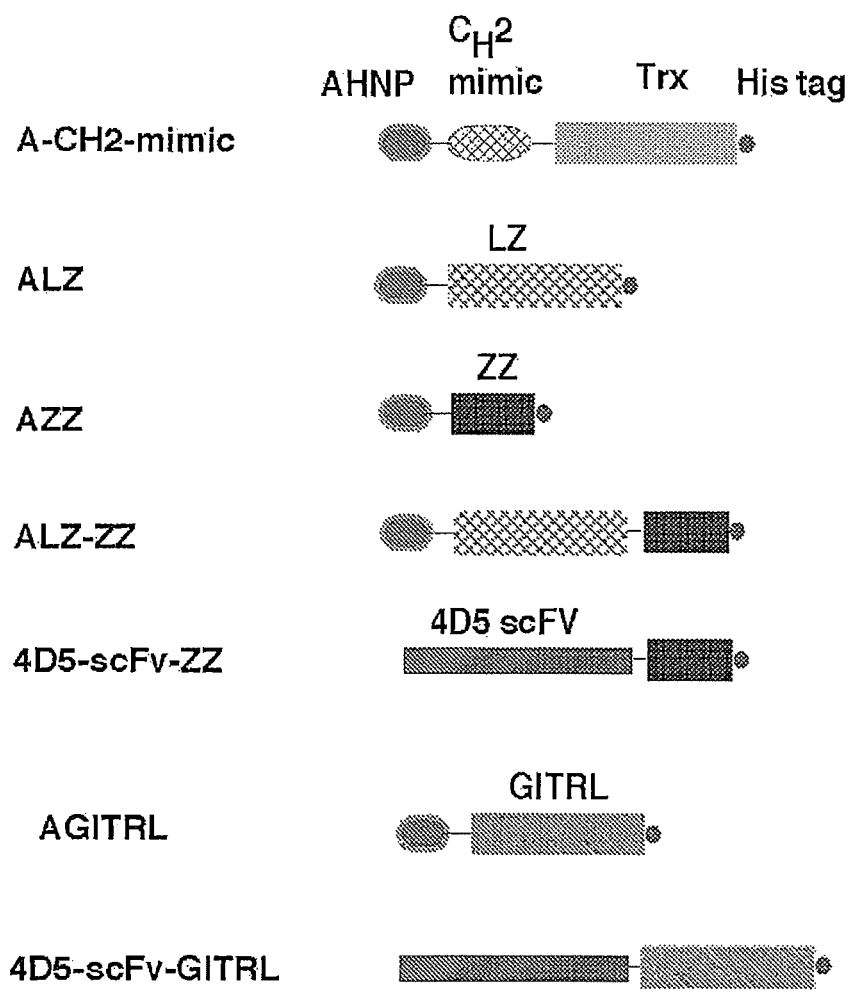

The anti-Her2/neu peptide (AHNP) was linked to a protein scaffolds to test several concepts for antigen-binding proteins. The antigen-binding protein constructs described herein (also referred to as small antibody surrogates (SAbS) or multifunctional antigen-binding proteins) have been constructed as fusion proteins having the AHNP or the 4D5scFv linked to the N-terminus of a scaffold, as illustrated in FIGS. 1(a) and 1(b). The AHNP-CH2 mimic (SEQ ID NO. 6) construct was made by linking AHNP with a peptide mimicking the CH2 domain of human IgG1 to which a Trx domain was added (SEQ ID NO. 2); the ALZ construct (SEQ ID NO. 5) was produced by conjugating AHNP to the N-terminus of the lucine-zipper (LZ) domain (SEQ ID NO. 1) of the human FOXP3 protein; the AZZ antigen-binding protein (SEQ ID NO. 7) was made by linking AHNP with a portion of Protein A, the ZZ scaffold, (SEQ ID NO. 3) that can interact with IgG; the AGITRL antigen-binding protein (SEQ ID NO. 8) was produced by linking AHNP to the N-terminus of the murine GITRL scaffold (SEQ ID NO. 4); the ALZ-ZZ antigen-binding protein (SEQ ID NO. 9) was constructed by linking the ZZ scaffold (SEQ ID NO. 3) to the C-terminus of the ALZ antigen-binding protein (SEQ ID NO. 5); 4D5-scFv-ZZ (SEQ ID NO. 10) was constructed by linking a ZZ domain (SEQ ID NO. 3) to the C-terminal end of the 4D5-scFv; and the 4D5-scFv-GITRL (SEQ ID NO. 11) was made by linking the murine GITRL domain (SEQ ID NO. 4) to the C-terminal end of the 4D5-scFv. All of these constructs can be expressed and purified with a poly-histidine epitope tag (His-tag).

EXAMPLE 2

Binding of AHNP Antigen-Binding Proteins to Fc Receptor

In some cases, antigen-binding protein can interact with an Fc receptor, which may facilitate cell-mediated cytotoxicity. Biacore experiments were conducted to determine whether the antigen-binding protein AHNP-CH2-mimic could bind to the FcγIIIB Fc receptor. The AHNP-CH2-mimic construct demonstrated a reasonable affinity for FcγIIIB with a Kd of ~50 µM. The interaction between AFc, an antigen binding protein consisting of AHNP linked to the Fc region of an IgG1 antibody, and FcγIIIB was examined for comparative purposes. The AFc-FcγIIIB interaction was observed to be weak and the affinity could not be quantified by Biacore. Since FcγIIIB is known to have low affinity to IgG1, the level of affinity observed for AHNP-CH2-mimic is very encouraging. Furthermore, a synthetic CH2-mimic peptide was also observed to compete with the monoclonal antibody 4D5 (IgG1) for binding to the FcγIIIB receptor when analyzed in Biacore experiments. Despite the observed competition for FcγIIIB, direct binding between the CH2-mimic peptide alone and FcγIIIB was not detected, possibly due to the inability for the interaction to be detected by Biacore.

The results from additional Biacore experiments suggests that the AHNP-CH2-mimic construct can bind to IgG1; however, the mechanism of this interaction is unclear and will require further investigation.

EXAMPLE 3

Binding of Antigen-Binding Proteins to Her2-Fc

Figure 2:
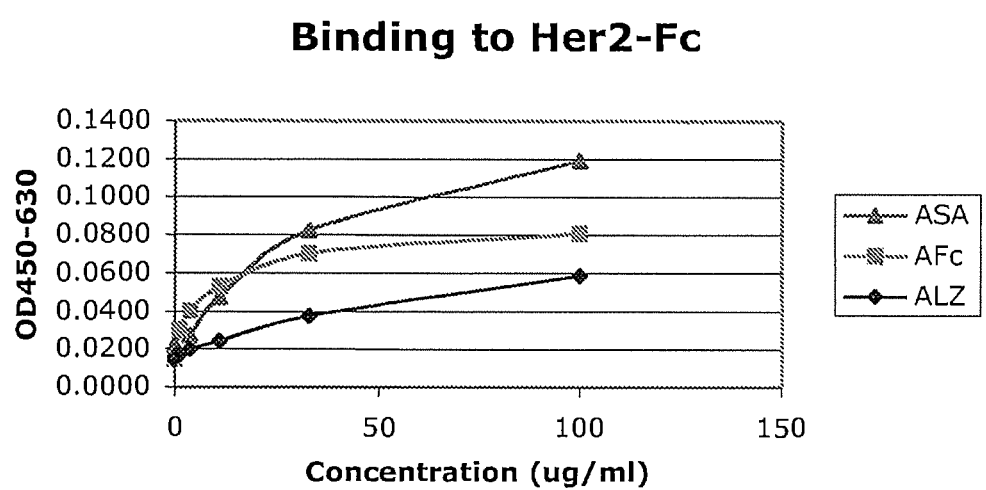
FIG. 2 provides a graphical representation of relative Her2-Fc binding for three antigen-binding proteins.

The ability of three antigen-binding proteins, ASA, AFc, and ALZ, to bind to Her2-Fc was examined by ELISA. The ASA constructs, used here for comparative purposes, was made by fusing the AHNP to a streptavidin (SA) scaffold and has been previously described (Masuda K, et al., Oncogene 25(59):7740-6 (2006)). Briefly, Her2-Fc was coated onto an ELISA plate at a concentration of 5 µg/ml. The antigen-binding proteins were then added to the plate at concentrations ranging from 1.2 to 100 µg/ml. Bound antigen-binding proteins were then detected using a rabbit anti-His tag antibody and HRP-conjugated anti-rabbit antibody. The results, depicted in FIG. 2, shows Her2-Fc specific binding for each construct (non-specific binding observed in control experiments has been subtracted).

EXAMPLE 4

Binding of AZZ to Her2-Fc

Figure 3:
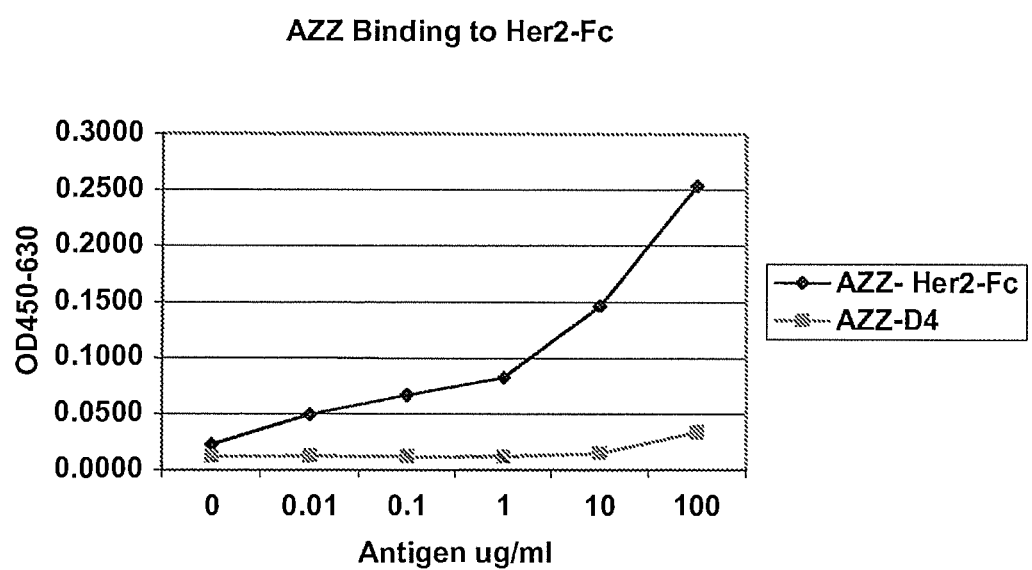
FIG. 3 depicts the relative binding activity of the AZZ antigen-binding protein to Her2 antigens with (Her2-Fc), or without (D4), an IgG-Fc domain.

The antigen-binding protein AZZ (SEQ ID NO. 7) was assessed for the ability to bind to Her2 constructs with and without the IgG-Fc domain. ELISA plates were coated with 5 µg/ml of either Her2-Fc or a recombinant form of domain 4 of the Her2 ectodomain (HER2 D4). The AZZ construct was then added to the plate at concentrations ranging from 0.01 to 100 µg/ml. Bound AZZ was detected using an anti-His tag antibody and an HRP-conjugated anti-rabbit antibody. The results of the experiments are illustrated in FIG. 3.

EXAMPLE 5

Binding of ALZ to T6-17 Cells

Figure 4:
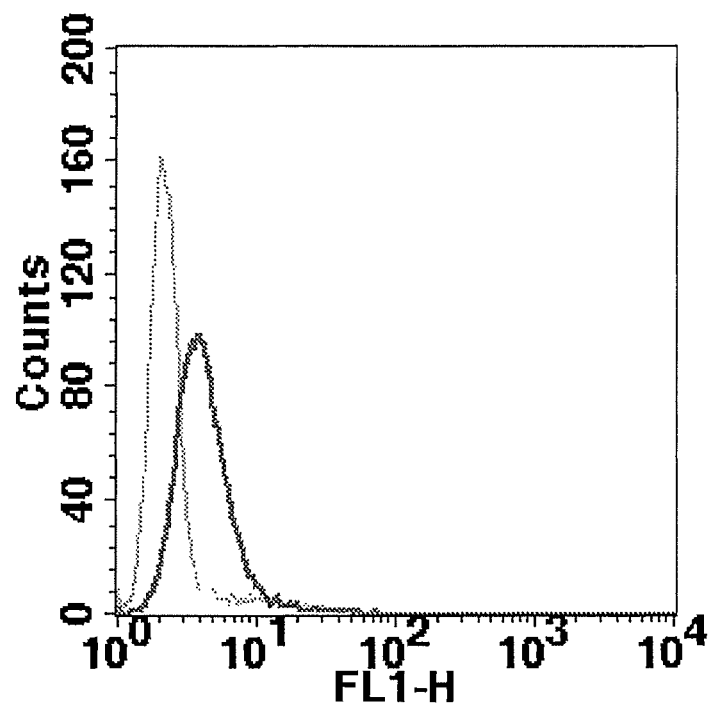
FIG. 4 illustrates binding of the ALZ antigen-specific peptide to T6-17 cells, which express the Her2/neu receptor.

Experiments were conducted to determine whether the ALZ construct (SEQ ID NO. 5) could bind to T6-17 cells, which express the Her2/neu receptor. T6-17 cells were incubated with (dark line) or without (light line) ALZ for 45 min on ice and then with a rabbit anti-His antibody followed by a FITC-labeled anti-rabbit antibody. Cells were analyzed by FACS and binding results are shown in FIG. 4. Other antigen-binding proteins were tested in this manner also. The AHNP-CH2-mimic (SEQ ID NO. 6) showed some ability to bind to T6-17 cells (data not shown), while AFc and AZZ (SEQ ID NO. 7) binding was not detected. These antigen-binding proteins also exhibited similar binding characteristics for the Her2/neu receptor expressed on the surface of SKBR3 cells (data not shown).

EXAMPLE 6

Inhibition of Tumor Growth

Figure 5:
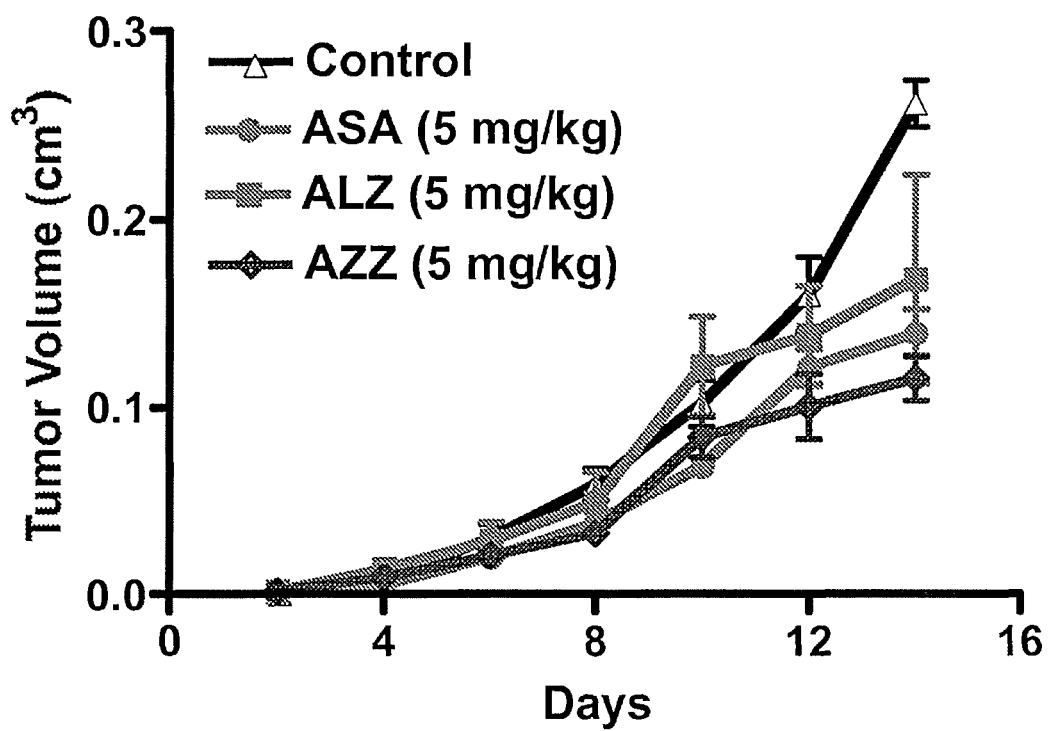
FIG. 5 shows the progression of tumor growth in mice injected with either the antigen-binding protein ASA, ALZ, or AZZ.

Several SABS constructs were tested for the ability to inhibit tumor growth using Ncr nu/nu athymic mice carrying T6-17 xenografts. Mice were injected intraperitoneally with either ASA, ALZ, or AZZ (5 mg/kg) antigen-binding proteins, and subsequent tumor growth was monitored for 14 days. Tumor size was determined with a digital caliper micrometer ruler. The resulting effect of the antigen-binding proteins on tumor growth is illustrated in FIG. 5. While the AZZ construct inhibited tumor growth, its binding affinity for the Her2/neu receptor is relatively low and can only be observed when more sensitive assays, such as ELISA, are used.

EXAMPLE 7

Production of Multifunctional Antigen-Binding Proteins

Figure 6:
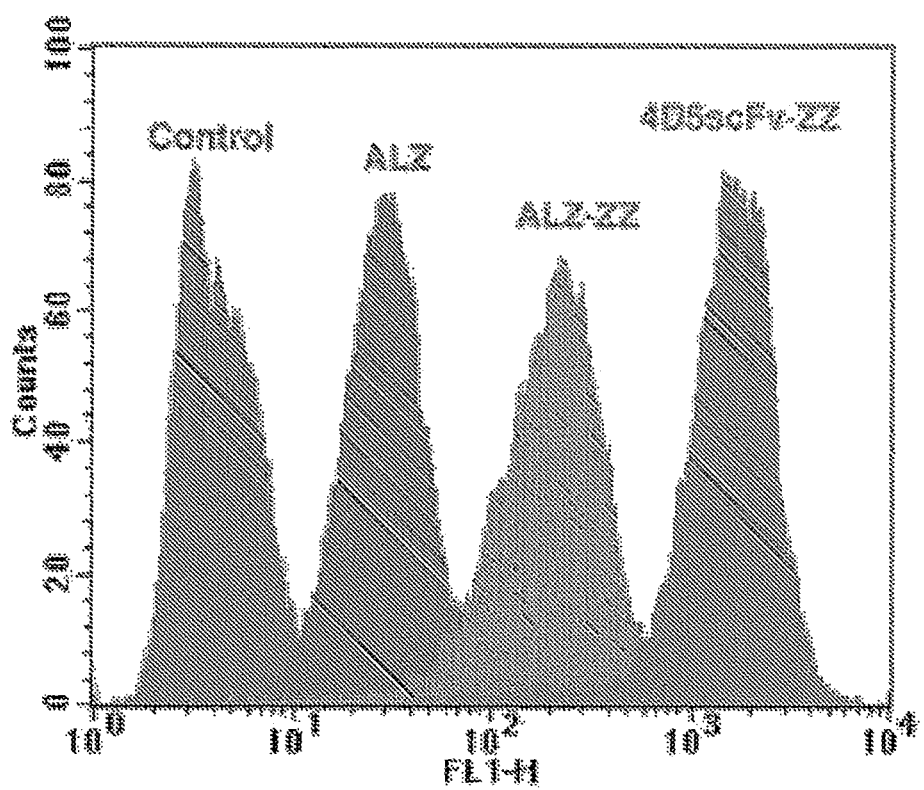
FIG. 6 demonstrates the ability of Her2/neu-specific antigen-binding proteins ALZ, AZZ, and 4D5scFv-ZZ to bind to the Her2/neu receptor expressed on the surface of SKBR3 cells.

Multifunctional antigen-binding proteins were expressed in *E. coli* BL21 strains after IPTG induction. Bacterial cultures were centrifuged and the cell pellets were separately resuspended in lysis buffer (20 mM sodium phosphate, 0.5 M NaCl, 30 mM Immidazole, 1 mM PMSF, 5 mM 2-ME, pH 7.4) and sonicated. Soluble multifunctional antigen-binding proteins, each of which have a his-tag, were purified by Ni-NTA chromatography. Insoluble proteins were solubilized in 8M urea, purified by Ni-NTA chromatography and then refolded by dialysis in a series of buffers with gradually lower urea concentration. Following production, experiments were conducted to determine the binding characteristics of the multifunctional antigen-binding proteins ALZ-ZZ (SEQ ID NO. 9) and 4D5scFv-ZZ (SEQ ID NO. 10), relative to other Her2/neu receptor binding proteins. FACS analysis was performed to assess the ability of ALZ, ALZ-ZZ, 4D5scFv-ZZ, and control buffer to bind to the Her2/neu receptor expressed on the surface of SKBR3 cells. The anti-His tag antibody and FITC-conjugated anti-rabbit antibody were used to detect the binding in the FACS assay. The relative binding activity of the tested antigen-binding proteins is illustrated in FIG. 6.

The affinity of 4D5scFv-ZZ for recombinantly expressed HER2 D4 and human IgG was also assessed using surface plasmon resonance analyses to determine dissociation constants ($K_d$) as described by Park et al. (Nature Biotechnology 18, 194-198 (2000)). As shown in Table 2, 4D5scFv-ZZ was observed to separately bind recombinantly expressed HER2 D4 and human IgG, while the 4D5scFv lacking a ZZ domain was unable to bind IgG.

TABLE 2

| Binding of 4D5scFv-ZZ to HER2/neu domain 4 and human IgG Dissociation constant ($K_d$ nM) | | |
|---|---|---|
| | HER2 D4 | Human IgG |
| 4D5scFv-ZZ | 112 | 1.3 |
| 4D5scFv | 145 | No binding |

EXAMPLE 8

Figure 7:
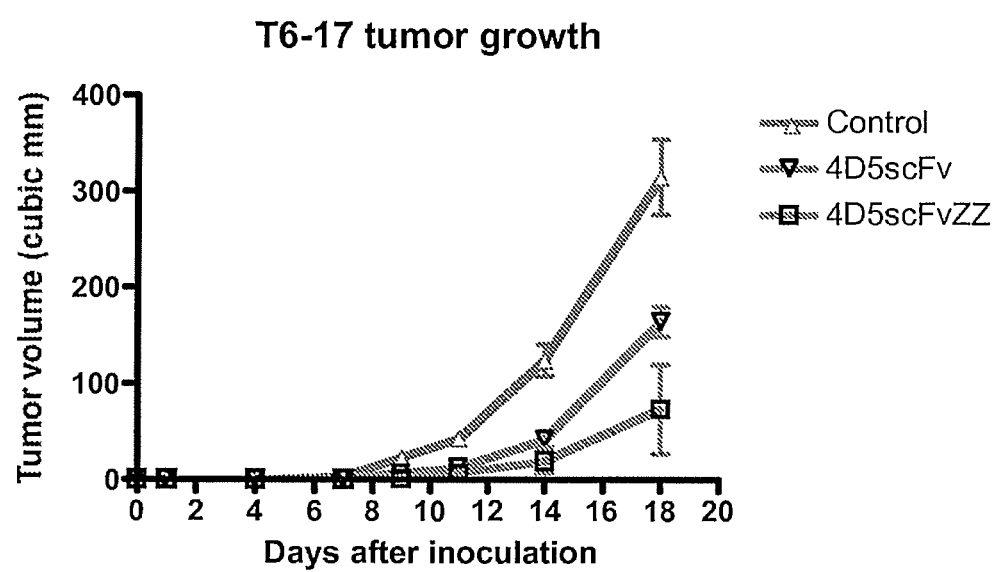
FIG. 7 shows the ability of 4D5scv-ZZ to inhibit tumor growth in vivo relative to 4D5scFv.

In Vivo Assessment of the Ability of Multifunctional Antigen-Binding Proteins to Inhibit Tumor Growth To determine whether a multifunctional antigen-binding protein could inhibit tumor growth in vivo, experiments were preformed to assess the affect of 4D5scFv-ZZ on tumors in mice. To conduct these studies, athymic nude mice were first injected with 50,000 T6-17 cells (NIH3T3 cells stably transfected with p185$^{HER2/neu}$ (Park, et el.)) to induce tumor formation. The mice were then treated with 10 mg/kg of either 4D5scFv-ZZ or 4D5scFv, while a control group of mice were inoculated with buffer only. Treatments were administered via intraperitoneal injection three times per week. Tumor growth was then assessed over a 16-day period. As shown in FIG. 7, mice treated with 4D5scFv-ZZ were observed to have the smallest tumors, while those injected with only buffer had the largest tumors.

Figure 8:
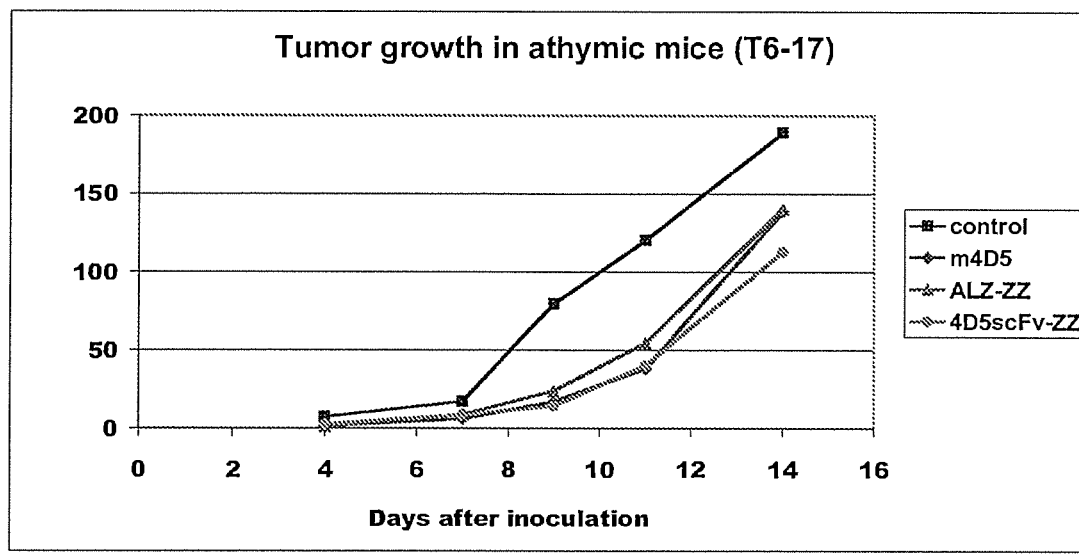
FIG. 8 shows the ability of 4D5scv-ZZ and ALZ-ZZ to inhibit tumor growth in vivo relative to the 4D5 monoclonal antibody.

Studies were also conducted to compare the ability of 4D5scFv-ZZ, ALZ-ZZ, and the 4D5 monoclonal antibody to inhibit tumor growth in mice (see, Park et al., describing the 4D5 antibody as Herceptin). In these experiments, athymic nude mice were injected with 1×10$^6$ T6-17 cells to induce tumor formation. Following a 3-4 day period to allow for the appearance of palpable tumors, the mice were treated with either 4D5scFv-ZZ (1.3 mg/kg), ALZ-ZZ (5 mg/kg), 4D5 monoclonal antibody (0.5 mg/kg), or buffer only (control). Mice were treated twice per week, beginning on day 1 of the assessment period, via intraperitoneal injection. As shown in FIG. 8, treated mice were all observed to have smaller tumors then control mice over a 14-day period. Collectively, these results indicate that multifunctional antigen-binding proteins are effective at inhibiting tumor growth in vivo.

What is claimed:

1. A multifunctional antigen-binding protein, comprising a glucocorticoid-induced tumor necrosis factor receptor ligand (GITRL) or a portion thereof and a 4D5 antibody-derived fragment single chain Fv region (4D5-scFv), wherein the multifunctional antigen-binding protein comprises the amino acid sequence of SEQ ID NO: 11.

2. The multifunctional antigen-binding protein of claim 1, wherein the GITRL is linked to the 4D5-scFv and is also capable of binding to a protein other than that bound by the 4D5-scFv.

3. The multifunctional antigen-binding protein of claim 1, wherein the GITRL comprises the amino acid sequence of SEQ ID NO: 4.

4. The multifunctional antigen-binding protein of claim 1, further comprising a protein domain that promotes solubility.

5. The multifunctional antigen-binding protein of claim 1, further comprising an epitope tag, a fluorophore, a radio isotope, or an enzyme.

6. The multifunctional antigen-binding protein of claim 5, wherein said epitope tag is a poly-histidine tag.

7. A polynucleotide encoding the multifunctional antigen-binding protein of claim 1.

8. A cell that has been genetically engineered to express the polynucleotide of claim 7.

9. A composition comprising the multifunctional antigen-binding protein claim 1 and a pharmaceutically acceptable carrier.

10. The multifunctional antigen-binding protein of claim 1, further comprising a linker having one or more glycine residues.

11. The multifunctional antigen-binding protein of claim 10, wherein the linker comprises SEQ ID NO: 25 or 26.

12. A method of treating a disease associated with Her2/neu expression in a subject comprising, administering a therapeutic amount of the multifunctional antigen-binding protein of claim 1 to the subject.

13. A method of detecting a Her2/neu receptor in a subject comprising, administering the multifunctional antigen-binding protein of claim 1 to the subject and detecting binding of the multifunctional antigen-binding protein to Her2/neu receptor.

14. A method of detecting the Her2/neu receptor, comprising exposing a sample containing the Her2/neu receptor to the multifunctional antigen-binding protein of claim 1 and detecting binding of the multifunctional antigen-binding protein to the sample.

* * * * *

SEQUENCE LISTING

<160> NUMBER OF SEQ ID NOS: 26

<210> SEQ ID NO 1
<211> LENGTH: 68
<212> TYPE: PRT
<213> ORGANISM: Artificial Sequence
<220> FEATURE:
<223> OTHER INFORMATION: Synthetic construct

<400> SEQUENCE: 1

Met Ala Ser Asp Phe Leu Lys His Cys Gln Ala Asp His Leu Leu Asp
1               5                   10                  15

Glu Lys Gly Arg Ala Gln Cys Leu Leu Gln Arg Glu Met Val Gln Ser
            20                  25                  30

Leu Glu Gln Gln Leu Val Leu Glu Lys Glu Lys Leu Ser Ala Met Gln
        35                  40                  45

Ala His Leu Ala Gly Lys Met Ala Leu Thr Lys Ala Ser Ser Val Ala
    50                  55                  60

Ser Ser Asp Lys
65

<210> SEQ ID NO 2
<211> LENGTH: 14
<212> TYPE: PRT
<213> ORGANISM: Artificial Sequence
<220> FEATURE:
<223> OTHER INFORMATION: Synthetic construct

<400> SEQUENCE: 2

Phe Pro Ala Pro Leu Ala Pro Gly Gly Leu Tyr Leu Gly Gly
1               5                   10

<210> SEQ ID NO 3
<211> LENGTH: 58
<212> TYPE: PRT
<213> ORGANISM: Artificial Sequence
<220> FEATURE:
<223> OTHER INFORMATION: Synthetic construct

<400> SEQUENCE: 3

Val Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 4
<211> LENGTH: 128
<212> TYPE: PRT
<213> ORGANISM: Artificial Sequence
<220> FEATURE:
<223> OTHER INFORMATION: Synthetic construct

<400> SEQUENCE: 4

Gln Leu Glu Thr Ala Lys Glu Pro Cys Met Ala Lys Phe Gly Pro Leu
1               5                   10                  15

Pro Ser Lys Trp Gln Met Ala Ser Ser Glu Pro Pro Cys Val Asn Lys
            20                  25                  30

Val Ser Asp Trp Lys Leu Glu Ile Leu Gln Asn Gly Leu Tyr Leu Ile

```
            35                  40                  45
Tyr Gly Gln Val Ala Pro Asn Ala Asn Tyr Asn Asp Val Ala Pro Phe
        50                  55                  60

Glu Val Arg Leu Tyr Lys Asn Lys Asp Met Ile Gln Thr Leu Thr Asn
 65                  70                  75                  80

Lys Ser Lys Ile Gln Asn Val Gly Gly Thr Tyr Glu Leu His Val Gly
                85                  90                  95

Asp Thr Ile Asp Leu Ile Phe Asn Ser Glu His Gln Val Leu Lys Asn
            100                 105                 110

Asn Thr Tyr Trp Gly Ile Ile Leu Leu Ala Asn Pro Gln Phe Ile Ser
            115                 120                 125

<210> SEQ ID NO 5
<211> LENGTH: 96
<212> TYPE: PRT
<213> ORGANISM: Artificial Sequence
<220> FEATURE:
<223> OTHER INFORMATION: Synthetic construct

<400> SEQUENCE: 5

Met Ala Phe Cys Asp Gly Phe Tyr Ala Cys Tyr Met Asp Val Gly Gly
 1               5                  10                  15

Gly Gly Gly Ser Met Ala Ser Asp Phe Leu Lys His Cys Gln Ala Asp
                20                  25                  30

His Leu Leu Asp Glu Lys Gly Arg Ala Gln Cys Leu Leu Gln Arg Glu
            35                  40                  45

Met Val Gln Ser Leu Glu Gln Gln Leu Val Leu Glu Lys Glu Lys Leu
        50                  55                  60

Ser Ala Met Gln Ala His Leu Ala Gly Lys Met Ala Leu Thr Lys Ala
 65                  70                  75                  80

Ser Ser Val Ala Ser Ser Asp Lys Leu Glu His His His His His His
                85                  90                  95

<210> SEQ ID NO 6
<211> LENGTH: 158
<212> TYPE: PRT
<213> ORGANISM: Artificial Sequence
<220> FEATURE:
<223> OTHER INFORMATION: Synthetic construct

<400> SEQUENCE: 6

Met Ala Phe Cys Asp Gly Phe Tyr Ala Cys Tyr Met Asp Val Gly Gly
 1               5                  10                  15

Gly Gly Gly Ser Phe Pro Ala Pro Leu Ala Pro Gly Gly Leu Tyr Leu
                20                  25                  30

Gly Gly Glu Asn Leu Tyr Phe Gln Gly Met Ser Asp Lys Ile Ile His
            35                  40                  45

Leu Thr Asp Asp Ser Phe Asp Thr Asp Val Leu Lys Ala Asp Gly Ala
        50                  55                  60

Ile Leu Val Asp Phe Trp Ala Glu Trp Cys Gly Pro Cys Lys Met Ile
 65                  70                  75                  80

Ala Pro Ile Leu Asp Glu Ile Ala Asp Glu Tyr Gln Gly Lys Leu Thr
                85                  90                  95

Val Ala Lys Leu Asn Ile Asp Gln Asn Pro Gly Thr Ala Pro Lys Tyr
            100                 105                 110

Gly Ile Arg Gly Ile Pro Thr Leu Leu Leu Phe Lys Asn Gly Glu Val
            115                 120                 125
```

```
Ala Ala Thr Lys Val Gly Ala Leu Ser Lys Gly Gln Leu Lys Glu Phe
            130                 135                 140

Leu Asp Ala Asn Leu Ala Leu Glu His His His His His His
145                 150                 155

<210> SEQ ID NO 7
<211> LENGTH: 86
<212> TYPE: PRT
<213> ORGANISM: Artificial Sequence
<220> FEATURE:
<223> OTHER INFORMATION: Synthetic construct

<400> SEQUENCE: 7

Met Ala Phe Cys Asp Gly Phe Tyr Ala Cys Tyr Met Asp Val Gly Gly
  1               5                  10                  15

Gly Gly Gly Ser Val Asp Asn Lys Phe Asn Lys Glu Gln Gln Asn Ala
             20                  25                  30

Phe Tyr Glu Ile Leu His Leu Pro Asn Leu Asn Glu Glu Gln Arg Asn
         35                  40                  45

Ala Phe Ile Gln Ser Leu Lys Asp Asp Pro Ser Gln Ser Ala Asn Leu
     50                  55                  60

Leu Ala Glu Ala Lys Lys Leu Asn Asp Ala Gln Ala Pro Lys Leu Glu
 65                  70                  75                  80

His His His His His His
             85

<210> SEQ ID NO 8
<211> LENGTH: 156
<212> TYPE: PRT
<213> ORGANISM: Artificial Sequence
<220> FEATURE:
<223> OTHER INFORMATION: Synthetic construct

<400> SEQUENCE: 8

Met Ala Phe Cys Asp Gly Phe Tyr Ala Cys Tyr Met Asp Val Gly Gly
  1               5                  10                  15

Gly Gly Gly Ser Gln Leu Glu Thr Ala Lys Glu Pro Cys Met Ala Lys
             20                  25                  30

Phe Gly Pro Leu Pro Ser Lys Trp Gln Met Ala Ser Ser Glu Pro Pro
         35                  40                  45

Cys Val Asn Lys Val Ser Asp Trp Lys Leu Glu Ile Leu Gln Asn Gly
     50                  55                  60

Leu Tyr Leu Ile Tyr Gly Gln Val Ala Pro Asn Ala Asn Tyr Asn Asp
 65                  70                  75                  80

Val Ala Pro Phe Glu Val Arg Leu Tyr Lys Asn Lys Asp Met Ile Gln
                 85                  90                  95

Thr Leu Thr Asn Lys Ser Lys Ile Gln Asn Val Gly Gly Thr Tyr Glu
            100                 105                 110

Leu His Val Gly Asp Thr Ile Asp Leu Ile Phe Asn Ser Glu His Gln
            115                 120                 125

Val Leu Lys Asn Asn Thr Tyr Trp Gly Ile Ile Leu Leu Ala Asn Pro
            130                 135                 140

Gln Phe Ile Ser Leu Glu His His His His His
145                 150                 155

<210> SEQ ID NO 9
<211> LENGTH: 161
<212> TYPE: PRT
<213> ORGANISM: Artificial Sequence
```

```
<220> FEATURE:
<223> OTHER INFORMATION: Synthetic construct

<400> SEQUENCE: 9

Met Ala Phe Cys Asp Gly Phe Tyr Ala Cys Tyr Met Asp Val Gly Gly
1               5                   10                  15

Gly Gly Gly Ser Met Ala Ser Asp Phe Leu Lys His Cys Gln Ala Asp
            20                  25                  30

His Leu Leu Asp Glu Lys Gly Arg Ala Gln Cys Leu Leu Gln Arg Glu
        35                  40                  45

Met Val Gln Ser Leu Glu Gln Gln Leu Val Leu Glu Lys Glu Lys Leu
50                  55                  60

Ser Ala Met Gln Ala His Leu Ala Gly Lys Met Ala Leu Thr Lys Ala
65                  70                  75                  80

Ser Ser Val Ala Ser Ser Asp Lys Gly Gly Gly Ser Glu Leu Val
            85                  90                  95

Asp Asn Lys Phe Asn Lys Glu Gln Gln Asn Ala Phe Tyr Glu Ile Leu
            100                 105                 110

His Leu Pro Asn Leu Asn Glu Glu Gln Arg Asn Ala Phe Ile Gln Ser
        115                 120                 125

Leu Lys Asp Asp Pro Ser Gln Ser Ala Asn Leu Leu Ala Glu Ala Lys
    130                 135                 140

Lys Leu Asn Asp Ala Gln Ala Pro Lys Leu Glu His His His His
145                 150                 155                 160

His

<210> SEQ ID NO 10
<211> LENGTH: 322
<212> TYPE: PRT
<213> ORGANISM: Artificial Sequence
<220> FEATURE:
<223> OTHER INFORMATION: Synthetic construct

<400> SEQUENCE: 10

Met Ala Asp Ile Gln Met Thr Gln Ser Pro Ser Ser Leu Ser Ala Ser
1               5                   10                  15

Val Gly Asp Arg Val Thr Ile Thr Cys Arg Ala Ser Gln Asp Val Asn
            20                  25                  30

Thr Ala Val Ala Trp Tyr Gln Gln Lys Pro Gly Lys Ala Pro Lys Leu
        35                  40                  45

Leu Ile Tyr Ser Ala Ser Phe Leu Tyr Ser Gly Val Pro Ser Arg Phe
    50                  55                  60

Ser Gly Ser Arg Ser Gly Thr Asp Phe Thr Leu Thr Ile Ser Ser Leu
65                  70                  75                  80

Gln Pro Glu Asp Phe Ala Thr Tyr Tyr Cys Gln Gln His Tyr Thr Thr
                85                  90                  95

Pro Pro Thr Phe Gly Gln Gly Thr Lys Val Glu Leu Lys Arg Ala Thr
            100                 105                 110

Pro Ser His Asn Ser His Gln Val Pro Ser Ala Gly Gly Pro Thr Ala
        115                 120                 125

Asn Ser Gly Glu Val Lys Leu Val Glu Ser Gly Gly Gly Leu Val Gln
    130                 135                 140

Pro Gly Gly Ser Leu Arg Leu Ser Cys Ala Thr Ser Gly Phe Asn Ile
145                 150                 155                 160

Lys Asp Thr Tyr Ile His Trp Val Arg Gln Ala Pro Gly Lys Gly Leu
                165                 170                 175
```

-continued

Glu Trp Val Ala Arg Ile Tyr Pro Thr Asn Gly Tyr Thr Arg Tyr Ala
                180                 185                 190

Asp Ser Val Lys Gly Arg Phe Thr Ile Ser Ala Asp Thr Ser Lys Asn
            195                 200                 205

Thr Ala Tyr Leu Gln Met Asn Ser Leu Arg Ala Glu Asp Thr Ala Val
        210                 215                 220

Tyr Tyr Cys Ser Arg Trp Gly Asp Gly Phe Tyr Ala Met Asp Tyr
225                 230                 235                 240

Trp Gly Gln Gly Thr Thr Val Thr Val Ser Ser Gly Gly Gly Gly Ser
                245                 250                 255

Val Asp Asn Lys Phe Asn Lys Glu Gln Gln Asn Ala Phe Tyr Glu Ile
            260                 265                 270

Leu His Leu Pro Asn Leu Asn Glu Glu Gln Arg Asn Ala Phe Ile Gln
        275                 280                 285

Ser Leu Lys Asp Asp Pro Ser Gln Ser Ala Asn Leu Leu Ala Glu Ala
    290                 295                 300

Lys Lys Leu Asn Asp Ala Gln Ala Pro Lys Leu Glu His His His His
305                 310                 315                 320

His His

<210> SEQ ID NO 11
<211> LENGTH: 392
<212> TYPE: PRT
<213> ORGANISM: Artificial Sequence
<220> FEATURE:
<223> OTHER INFORMATION: Synthetic construct

<400> SEQUENCE: 11

Met Ala Asp Ile Gln Met Thr Gln Ser Pro Ser Ser Leu Ser Ala Ser
1               5                   10                  15

Val Gly Asp Arg Val Thr Ile Thr Cys Arg Ala Ser Gln Asp Val Asn
            20                  25                  30

Thr Ala Val Ala Trp Tyr Gln Gln Lys Pro Gly Lys Ala Pro Lys Leu
        35                  40                  45

Leu Ile Tyr Ser Ala Ser Phe Leu Tyr Ser Gly Val Pro Ser Arg Phe
    50                  55                  60

Ser Gly Ser Arg Ser Gly Thr Asp Phe Thr Leu Thr Ile Ser Ser Leu
65                  70                  75                  80

Gln Pro Glu Asp Phe Ala Thr Tyr Tyr Cys Gln Gln His Tyr Thr Thr
                85                  90                  95

Pro Pro Thr Phe Gly Gln Gly Thr Lys Val Glu Leu Lys Arg Ala Thr
            100                 105                 110

Pro Ser His Asn Ser His Gln Val Pro Ser Ala Gly Gly Pro Thr Ala
        115                 120                 125

Asn Ser Gly Glu Val Lys Leu Val Glu Ser Gly Gly Gly Leu Val Gln
    130                 135                 140

Pro Gly Gly Ser Leu Arg Leu Ser Cys Ala Thr Ser Gly Phe Asn Ile
145                 150                 155                 160

Lys Asp Thr Tyr Ile His Trp Val Arg Gln Ala Pro Gly Lys Gly Leu
                165                 170                 175

Glu Trp Val Ala Arg Ile Tyr Pro Thr Asn Gly Tyr Thr Arg Tyr Ala
            180                 185                 190

Asp Ser Val Lys Gly Arg Phe Thr Ile Ser Ala Asp Thr Ser Lys Asn
        195                 200                 205

```
Thr Ala Tyr Leu Gln Met Asn Ser Leu Arg Ala Glu Asp Thr Ala Val
210                 215                 220
Tyr Tyr Cys Ser Arg Trp Gly Asp Gly Phe Tyr Ala Met Asp Tyr
225                 230                 235                 240
Trp Gly Gln Gly Thr Thr Val Thr Val Ser Ser Gly Gly Gly Ser
                245                 250                 255
Gln Leu Glu Thr Ala Lys Glu Pro Cys Met Ala Lys Phe Gly Pro Leu
            260                 265                 270
Pro Ser Lys Trp Gln Met Ala Ser Ser Glu Pro Pro Cys Val Asn Lys
            275                 280                 285
Val Ser Asp Trp Lys Leu Glu Ile Leu Gln Asn Gly Leu Tyr Leu Ile
290                 295                 300
Tyr Gly Gln Val Ala Pro Asn Ala Asn Tyr Asn Asp Val Ala Pro Phe
305                 310                 315                 320
Glu Val Arg Leu Tyr Lys Asn Lys Asp Met Ile Gln Thr Leu Thr Asn
                325                 330                 335
Lys Ser Lys Ile Gln Asn Val Gly Gly Thr Tyr Glu Leu His Val Gly
            340                 345                 350
Asp Thr Ile Asp Leu Ile Phe Asn Ser Glu His Gln Val Leu Lys Asn
            355                 360                 365
Asn Thr Tyr Trp Gly Ile Ile Leu Leu Ala Asn Pro Gln Phe Ile Ser
370                 375                 380
Leu Glu His His His His His His
385                 390

<210> SEQ ID NO 12
<211> LENGTH: 12
<212> TYPE: PRT
<213> ORGANISM: Artificial Sequence
<220> FEATURE:
<223> OTHER INFORMATION: Synthetic construct

<400> SEQUENCE: 12

Phe Cys Asp Gly Phe Tyr Ala Cys Tyr Met Asp Val
1               5                   10

<210> SEQ ID NO 13
<211> LENGTH: 12
<212> TYPE: PRT
<213> ORGANISM: Artificial Sequence
<220> FEATURE:
<223> OTHER INFORMATION: Synthetic construct

<400> SEQUENCE: 13

Tyr Cys Asp Gly Phe Tyr Ala Cys Tyr Met Asp Val
1               5                   10

<210> SEQ ID NO 14
<211> LENGTH: 11
<212> TYPE: PRT
<213> ORGANISM: Artificial Sequence
<220> FEATURE:
<223> OTHER INFORMATION: Synthetic construct

<400> SEQUENCE: 14

Tyr Cys Phe Pro Asp Glu Glu Gly Ala Cys Tyr
1               5                   10

<210> SEQ ID NO 15
<211> LENGTH: 30
<212> TYPE: PRT
```

<213> ORGANISM: Artificial Sequence
<220> FEATURE:
<223> OTHER INFORMATION: Synthetic construct

<400> SEQUENCE: 15

```
Pro Cys Pro Ile Asn Cys Thr His Ser Cys Val Asp Leu Asp Lys
1               5                   10                  15

Gly Cys Pro Ala Glu Gln Arg Ala Ser Pro Leu Thr Ser Ile
            20                  25                  30
```

<210> SEQ ID NO 16
<211> LENGTH: 13
<212> TYPE: PRT
<213> ORGANISM: Artificial Sequence
<220> FEATURE:
<223> OTHER INFORMATION: Synthetic construct

<400> SEQUENCE: 16

```
Tyr Cys Pro Ile Trp Lys Phe Pro Asp Glu Glu Cys Tyr
1               5                   10
```

<210> SEQ ID NO 17
<211> LENGTH: 11
<212> TYPE: PRT
<213> ORGANISM: Artificial Sequence
<220> FEATURE:
<223> OTHER INFORMATION: Synthetic construct

<400> SEQUENCE: 17

```
Tyr Cys Phe Pro Asp Glu Glu Gly Ala Cys Tyr
1               5                   10
```

<210> SEQ ID NO 18
<211> LENGTH: 14
<212> TYPE: PRT
<213> ORGANISM: Artificial Sequence
<220> FEATURE:
<223> OTHER INFORMATION: Synthetic construct

<400> SEQUENCE: 18

```
Tyr Cys Gly Tyr Ser Ser Thr Ser Tyr Cys Phe Val Met Asp
1               5                   10
```

<210> SEQ ID NO 19
<211> LENGTH: 16
<212> TYPE: PRT
<213> ORGANISM: Artificial Sequence
<220> FEATURE:
<223> OTHER INFORMATION: Synthetic construct

<400> SEQUENCE: 19

```
Tyr Cys Ala Ser Arg Asp Tyr Asp Tyr Asp Gly Arg Cys Tyr Phe Asp
1               5                   10                  15
```

<210> SEQ ID NO 20
<211> LENGTH: 16
<212> TYPE: PRT
<213> ORGANISM: Artificial Sequence
<220> FEATURE:
<223> OTHER INFORMATION: Synthetic construct

<400> SEQUENCE: 20

```
Tyr Cys Thr Arg Gly Tyr Ser Ser Thr Ser Tyr Cys Tyr Ala Met Asp
1               5                   10                  15
```

<210> SEQ ID NO 21

```
<211> LENGTH: 12
<212> TYPE: PRT
<213> ORGANISM: Artificial Sequence
<220> FEATURE:
<223> OTHER INFORMATION: Synthetic construct

<400> SEQUENCE: 21

Phe Cys Met Glu Glu Ser Gly Gly Asn Tyr Cys Tyr
1               5                   10

<210> SEQ ID NO 22
<211> LENGTH: 13
<212> TYPE: PRT
<213> ORGANISM: Artificial Sequence
<220> FEATURE:
<223> OTHER INFORMATION: Synthetic construct

<400> SEQUENCE: 22

Tyr Cys Ala Leu Arg Gly Gly Val Tyr Trp Pro Cys Tyr
1               5                   10

<210> SEQ ID NO 23
<211> LENGTH: 14
<212> TYPE: PRT
<213> ORGANISM: Artificial Sequence
<220> FEATURE:
<223> OTHER INFORMATION: Synthetic construct

<400> SEQUENCE: 23

Tyr Cys Ala Leu Thr Tyr Tyr Asp Tyr Glu Cys Phe Ala Tyr
1               5                   10

<210> SEQ ID NO 24
<211> LENGTH: 13
<212> TYPE: PRT
<213> ORGANISM: Artificial Sequence
<220> FEATURE:
<223> OTHER INFORMATION: Synthetic construct

<400> SEQUENCE: 24

Tyr Cys Leu Val Trp Lys Tyr Ala Asp Ala Gly Cys Tyr
1               5                   10

<210> SEQ ID NO 25
<211> LENGTH: 5
<212> TYPE: PRT
<213> ORGANISM: Artificial Sequence
<220> FEATURE:
<223> OTHER INFORMATION: Synthetic construct

<400> SEQUENCE: 25

Gly Gly Gly Gly Ser
1               5

<210> SEQ ID NO 26
<211> LENGTH: 6
<212> TYPE: PRT
<213> ORGANISM: Artificial Sequence
<220> FEATURE:
<223> OTHER INFORMATION: Synthetic construct

<400> SEQUENCE: 26

Gly Gly Gly Gly Gly Ser
1               5
```